United States Patent
Ermantraut et al.

(10) Patent No.: US 9,791,441 B2
(45) Date of Patent: Oct. 17, 2017

(54) DEVICE AND METHOD FOR THE DETECTION OF PARTICLES

(71) Applicant: CLONDIAG GMBH, Jena (DE)

(72) Inventors: Eugen Ermantraut, Jena (DE); Ralf Bickel, Jena (DE); Torsten Schulz, Jena (DE); Thomas Ullrich, Jena (DE); Jens Tuchscheerer, Jena (DE)

(73) Assignee: CLONDIAG GMBH, Jena (DE)

( * ) Notice: Subject to any disclaimer, the term of this patent is extended or adjusted under 35 U.S.C. 154(b) by 0 days.

(21) Appl. No.: 13/919,524

(22) Filed: Jun. 17, 2013

(65) Prior Publication Data

US 2013/0295657 A1 Nov. 7, 2013

Related U.S. Application Data

(63) Continuation of application No. 13/274,175, filed on Oct. 14, 2011, now Pat. No. 8,467,039, which is a (Continued)

(30) Foreign Application Priority Data

Nov. 4, 2005 (DE) ........................ 10 2005 052 752

(51) Int. Cl.
*G01N 21/00* (2006.01)
*G01N 33/569* (2006.01)
(Continued)

(52) U.S. Cl.
CPC .... *G01N 33/56966* (2013.01); *B01F 11/0045* (2013.01); *B01F 11/0266* (2013.01);
(Continued)

(58) Field of Classification Search
CPC .......... G01N 21/00; G01N 1/10; G01N 21/03
(Continued)

(56) References Cited

U.S. PATENT DOCUMENTS 4,818,104 A * 4/1989 Hartman ................ G01B 11/26
356/138
5,576,827 A * 11/1996 Strickland .......... G01N 15/0211
356/336

(Continued)

FOREIGN PATENT DOCUMENTS

EP 0 891 811 A1 1/1999
FR 2 803 225 A1 7/2001
(Continued)

OTHER PUBLICATIONS

Dongeun, Huh, et al., "Microfluidics for flow cytometric analysis of cells and particles," *Institute of Physics Publishing Physiol. Meas.* (2005) vol. 26 pp. R73-R98.

*Primary Examiner* — Roy M Punnoose
(74) *Attorney, Agent, or Firm* — Steptoe & Johnson LLP

(57) ABSTRACT

The present invention relates to devices and methods for the qualitative and/or quantitative detection of particles. In particular, the invention relates to devices for the detection of particles, comprising a reaction chamber formed within a chamber body between a first surface and a second surface, wherein the second surface is located opposite to the first surface, and one or more displacers, wherein the distance between the first surface and the second surface is variable via the one or more displacers at least in one or more parts of the surface area of the first surface and/or second surface. The invention also relates to corresponding methods for the detection of particles.

15 Claims, 7 Drawing Sheets

Related U.S. Application Data continuation of application No. 12/092,422, filed as application No. PCT/EP2006/068153 on Nov. 6, 2006, now Pat. No. 8,040,494.

(51) Int. Cl.

| | | |
|---|---|---|
| *B01F 11/00* | (2006.01) | |
| *B01F 11/02* | (2006.01) | |
| *B01F 13/00* | (2006.01) | |
| *B01L 3/00* | (2006.01) | |
| *G01N 21/03* | (2006.01) | |
| *G01N 35/00* | (2006.01) | |

(52) U.S. Cl.
CPC ...... *B01F 13/0059* (2013.01); *B01L 3/50273* (2013.01); *B01L 3/502746* (2013.01); *G01N 21/03* (2013.01); *B01L 2200/027* (2013.01); *B01L 2300/0636* (2013.01); *B01L 2300/0822* (2013.01); *B01L 2300/0825* (2013.01); *B01L 2400/0481* (2013.01); *G01N 35/0099* (2013.01); *G01N 2021/0346* (2013.01); *G01N 2035/00346* (2013.01)

(58) Field of Classification Search
USPC .................................. 356/71, 337, 338, 246
See application file for complete search history.

(56) References Cited

U.S. PATENT DOCUMENTS

| | | | | |
|---|---|---|---|---|
| 5,690,895 | A | * | 11/1997 | Matsumoto ........ G01N 15/1404 356/246 |
| 7,701,643 | B2 | * | 4/2010 | Batchko ............... G02B 26/005 359/665 |
| 8,040,494 | B2 | * | 10/2011 | Ermantraut ......... B01F 11/0045 356/71 |
| 2007/0206203 | A1 | * | 9/2007 | Trainer .................. G01B 11/08 356/521 |
| 2007/0242269 | A1 | * | 10/2007 | Trainer .............. G01N 15/0205 356/336 |
| 2007/0243523 | A1 | * | 10/2007 | Ionescu-Zanetti B01L 3/502738 435/4 |
| 2008/0221711 | A1 | * | 9/2008 | Trainer .............. G01N 15/0205 700/54 |
| 2008/0231963 | A1 | * | 9/2008 | Batchko ............... G02B 26/005 359/665 |

FOREIGN PATENT DOCUMENTS

| | | |
|---|---|---|
| WO | WO 03/015923 | 2/2003 |
| WO | WO 03/022435 | 3/2003 |
| WO | WO 2005091970 A2 * | 10/2005 |

\* cited by examiner

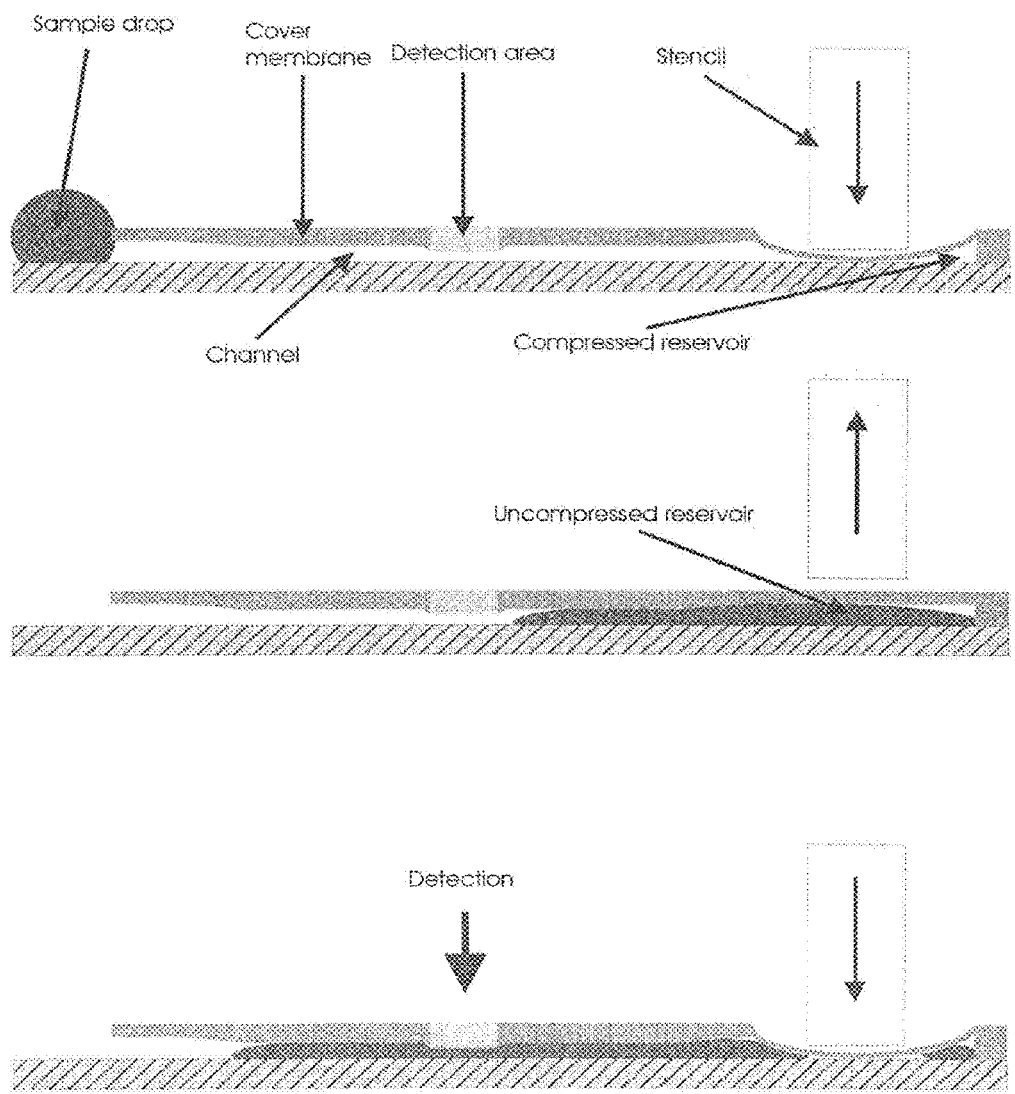

Results of assay for determining the number of CD4+ cells in human blood

DEVICE AND METHOD FOR THE DETECTION OF PARTICLES

CLAIM OF PRIORITY

This application claims priority to and is a continuation of U.S. application Ser. No. 13/274,175, filed Oct. 14, 2011, which claims priority to U. S. application Ser. No. 12/092,422, filed May 2, 2008, which claims priority under 35 USC §371 to International Application No. PCT/EP2006/068153, filed on Nov. 6, 2006, which claims priority to German Application Ser. No. 10 2005 052 752.3, filed Nov. 4, 2005, each of which is incorporated by reference in its entirety.

RELATED APPLICATIONS

This application claims the benefit of German patent application DE 10 2005 052 752, which is incorporated herein by reference in its entirety. The present application further relates to German patent application DE 10 2005 052 713 and to the International Patent Application entitled "Method and device for the detection of molecular interactions", filed on Nov. 6, 2006 (Maiwald reference number: C 7794), both of which applications are incorporated herein by reference in their entireties.

FIELD OF THE INVENTION

The invention relates to devices and methods for the detection of particles.

BACKGROUND

The detection of the presence and/or the enumeration of absolute levels of one or more species of particles like cells or viruses in samples such as human and non-human body fluids is of primary importance in determining the state of health of human beings and mammals in general. Clinically important examples of such applications involve counting of CD4+ cells in HIV-positive subjects, of granulocytes and platelets in patients treated with chemotherapy, and of leukocytes in blood bags. Non-medical applications, on the other hand, include the detection of (bacterial) contaminants in environmental samples such as sewage or in food products.

The main analytical platform for performing such analyses is currently flow cytometry-based assay systems. Flow cytometry involves the delivery of a flowing stream containing a sample having target particles therein to the detection region of a flow cytometer. The particles are arranged in single file along a core stream using hydrodynamic focusing within a sheath fluid. The particles are then individually interrogated by a light beam. Typically, the target particles in the detection region are irradiated using a laser to create an illumination phenomenon by the target particles. The optics and detection electronics measure the light absorption, scattering, fluorescence, and/or spectral properties of the target particles in the sample, or alternatively, the respective properties of a fluorescent label attached to the target particles. In case of fluorescence, each target particle produces a burst of fluorescence photons as it passes through the illumination region. Furthermore, differentiation of the fluorescence from the illumination or the excitation light can be accomplished with a filter or a combination of filters. Detection of the fluorescence is achieved using a photomultiplier tube or a photodiode. Another technique relies on light scattering of photons in the illumination beam by the target particle. The target particle is identified by its light scattering as a function of the angle of scattering, which is, in turn, a function of its size and shape as well as the wavelength of the scattered photons.

Thus, the successful detection and identification of a single target particle depends upon several factors. First, the laser power must be sufficient to generate a large enough number of fluorescence (or alternatively scattering) photons during the brief passage of the target particle through the irradiation region. Detection of the particle typically occurs when the a sufficient number of photons is generated so that the fluorescent burst from the target particle is reliably differentiated from random fluctuations of background photons. Second, it is important to minimize these unwanted background photons arising from scattering or from fluorescence emitted by the carrier liquid of the sample or impurities in the liquid, as well as from the apparatus itself, such as the walls of the capillary through which the flow stream passes.

Flow cytometers and methods for their use in different applications are described, for example, in Sharpiro, R. M. (2002) Practical Flow Cytometry, 4th ed., Wiley-Liss, New York. N.Y.; as well as inter alia in WO 90/13368. WO 99/44037, and WO 01/59429.

However, conventional flow cytometry systems remain largely inaccessible for routine clinical use due to typically bulky instrumentation, which does not only make "on-site" measurements (e.g. bedside testing) difficult but also gives rise to high costs per analysis. Thus, there is a clear need for simpler, more compact and less expensive systems, preferably exhibiting comparable performance characteristics.

Accordingly, in recent years microfluidic techniques have been employed for the purposes of developing cytometers which require smaller sample and reagent volumes (see, e.g., Altendorf. E. et al. (1997) *Sens. Actual.* 1, 531-534; Huh, D. et al. (2005) *Physiol. Meas.* 26, R73-R98; Dittrich, P. S., and Manz, A. (2005) *Anal. Bioanal. Chem.* 382, 1771-1782). Analytical instruments based on these efforts are smaller and more portable than conventional devices.

An example of such a miniaturized flow cytometer is described in the International Patent Application WO 02/10713. This device uses a non-precision fluid driver that is coupled to the sample fluid receiver and the reservoirs for supporting fluids, respectively, and controlled by a closed loop feedback path, thus enabling a more compact instrumental setup.

Instead of using flow cytometry it is also possible to determine the presence and/or number of particles in a given sample in an indirect manner by employing molecular markers (i.e. labels) that are specific for the particles of interest, and whose copy number in the sample correlates with that of the particles. Currently, different approaches are available to perform such analyses, for example ELISA-based assays (see, e.g., Kannangal, R. et al. (2001) *Clin. Diagn. Lab. Immunol.* 8, 1286-1288) as well as microscope-based methods involving the use of coated paramagnetic beads (see, e.g., Carella, A. Y. et al. (1995) *Clin. Diagn. Lab. Immunol.* 2, 623-625) or coated latex beads (see, e.g., Balakrishnan. P. et al (2004) *J. Acquir. Immune Defic. Syndr.* 36, 1006-1010). Furthermore, it is also possible to specifically capture the labeled particles on a membrane before imaging them using microscope optics (Rodriguez, W. R. et al. (2005) *PLOS Medicine* 2, e182, 663-672).

Another type of assay devices for counting particles is described in the International Patent Application WO 2005/008226. The device comprises a light source projecting light into a sub-area of a sample chip containing the particles to be analyzed labeled with a dye, and a shifter for shifting the position of the chip by a predetermined distance at every predetermined time interval relative to the object lens and the light source, respectively, in such a way that a certain area adjacent to the area photographed just before is shifted to the point where the light is incident. Therefore, sub-areas on the sample chip are photographed successively. The number of particles in each sub-area is counted and mathematically processed to calculate the total number of particles in the sample.

Furthermore, the U.S. Patent Application 2006/0024756 relates to a compact imaging cytometry device for the detection of magnetically labeled target particles or cells. For that purpose, all cells present in a biological sample to be analyzed are fluorescently labeled, but only the target cells are also magnetically labeled using a monoclonal antibody coupled to ferromagnetic beads. The labeled sample, in a chamber or cuvette, is placed between two wedge-shaped magnets to selectively move the magnetically labeled cells to the observation surface of the cuvette. An LED illuminates the cells and a CCD camera captures the images of the fluorescent light emitted by the target cells. Digital image analysis provides a count of the cells on the surface that can be related to the target cell concentration of the original sample.

However, all these devices and methods described above require comparably sophisticated detection techniques, which are expensive both in terms of initial cost and maintenance of the necessary analytical instrumentation as well as require highly trained personnel. This makes the conventional systems unsuitable for routine medical practices, "bedside" testing, or in remote locations.

Thus, there still remains a need for assay devices for the qualitative and/or quantitative detection of one or more particles in a sample, which overcome the above-mentioned limitations. In particular, there is a need for devices enabling the detection even of small amounts (i.e. numbers) of a given particle not only with high sensitivity but also in an easy-to-do and cost-efficient manner.

Furthermore, there is also a need for corresponding methods using such assay devices for the rapid and reliable detection of the presence and/or the accurate determination of the amount of one or more species of particles in a given sample. In particular, there is a need for methods that can be performed "on-site", i.e. during or immediately after collecting the sample to be analyzed.

Accordingly, it is an object of the present invention to provide such assay devices as well as the corresponding methods using the same.

SUMMARY OF THE INVENTION

In a first aspect, the present invention relates to a device for the qualitative and/or quantitative detection of particles, comprising a reaction chamber formed within a chamber body between a first surface and a second surface, wherein the second surface is located opposite to the first surface; and one or more displacers, wherein the distance between the first surface and the second surface is variable via the one or more displacers at least in one or more parts of the surface area of the first surface and/or the second surface.

The one or more displacers may be integral parts of the first surface and/or of the second surface ("displacement structures") or may be self-contained entities ("displacement bodies") located opposite to the first surface and/or of the second surface. The one or more displacers may be made of an elastically deformable material. In a preferred embodiment, the device comprises two displacers, which may be located opposite either to the same or to different surfaces.

Preferably, at least a part of the first and/or the second surface is/are made of a transparent material. Furthermore, it is preferred that at least one or more parts of the first surface and/or of the second surface is/are elastically deformable. Particularly preferably, the at least one or more elastically deformable parts are located opposite to the one or more displacers. The at least one or more elastically deformable parts may be different from the surface area where detection takes place.

In some embodiments, the device of the invention further comprises one or more means, which, when the reaction chamber is elastically deformed, allow keeping the volume of the reaction chamber essentially constant. Preferably, the one or more means are elastic sidewalls laterally delimiting the reaction chamber.

In a further aspect, the present invention relates to a system, comprising at least two parts, wherein each of the at least two parts comprises a reaction chamber formed within a chamber body between a first surface and a second surface, wherein the second surface is located opposite to the first surface; and one or more displacers, wherein the distance between the first surface and the second surface is variable via the one or more displacers at least in one or more parts of the surface area of the first surface and/or the second surface; and wherein the reaction chambers of the at least two parts are in communication with each other.

The reaction chamber, the first surface, the second surface and/or the at least one displacer of a part of the system may be formed as described for the inventive device.

In one embodiment, the system further comprises one or more means, which, when the reaction chamber is elastically deformed, allow keeping the volume of the reaction chamber essentially constant. Preferably, the one or more means are elastic sidewalls laterally delimiting the reaction chamber.

In another embodiment, the system further comprises a detection system.

Particularly preferably, the system further comprises a sample introduction passage in communication with each of the reaction chambers of the at least two devices and optionally also one or more means that allow for a transient fluid communication between the at least two reaction chambers.

In a further aspect, the present invention relates to a method for the qualitative and/or quantitative detection of particles, comprising positioning a sample supposed to comprise one or more species of particles to be detected in a reaction chamber, displacing at least a part of the sample within the reaction chamber via the one or more displacers, and detecting/determining a value indicative for the presence and/or number of one or more species of particles.

Preferably, the sample to be analyzed is a biological sample, and the one or more species of particles to be detected are selected from the group consisting of prokaryotic cells, eukaryotic cells, and viral particles.

In a preferred embodiment, positioning the sample in a reaction chamber comprises introducing said sample into the reaction chamber of a device according to the present invention.

Preferably, the at least part of the sample is displaced by varying, particularly preferably by reducing, the distance between the first surface and the second surface at least in one or more parts of the surface area of the first surface and/or the second surface by applying pressure to the first surface and/or the second surface via at least one of the one or more displacers.

In a preferred embodiment of the inventive method, after displacing at least part of the sample the reduced distance is subsequently re-increased. This reduction and subsequent re-increase of the distance may be performed repeatedly. Detection is preferably performed after the distance between the first surface and the second surface has been reduced.

In one embodiment, the method of the invention comprises positioning a sample comprising multiple particles in a reaction chamber, displacing a subset of said multiple particles within the reaction chamber via the one or more displacers, determining one or more values indicative for the number of the subset of particles displaced within the reaction chamber, and optionally calculating the total number of the multiple particles in the reaction chamber from the one or more values obtained during detection.

In some embodiments, the method further comprises positioning/introducing one or more agents each comprising one or more detectable moieties into the reaction chamber before performing detection. Preferably, the one or more agents are selected from the group consisting of nucleic acids, peptides, protein domains, proteins, carbohydrates, low molecular weight chemical compounds, and analogs and/or mixtures thereof and have binding affinity for one or more particles to be detected.

In a further aspect, the invention relates to a method comprising positioning multiple particles of a sample within a detection chamber, displacing some of the multiple particles from the detection chamber so that only a proper subset of the multiple particles remains, optically detecting particles of the subset of multiple particles, and based on the detected particles, determining a value indicative of the number of panicles of the subset of particles.

In one embodiment, the method further comprises determining a value indicative of a number or abundance of panicles in the sample based on the value indicative of the number of particles of the proper subset. Optionally, this determination is further based on a size of a detection volume of the detection chamber.

In preferred embodiments, the method further comprises repeating a number NR times the steps of positioning multiple particles of the sample within the detection chamber and displacing some of the multiple particles from the detection chamber so that, in each case, only a proper subset of the multiple particles remains, and where NR≥2 and, for a number ND of the NR repetitions, optically detecting particles of the subset of multiple particles and, based on the detected particles, determining a value indicative of the number of particles of the proper subset of particles, where ND≥NR.

In further preferred embodiments of the inventive method, repeating the number NR times the steps of positioning and displacing comprises, for multiple of the NR repetitions, reintroducing at least some of the displaced multiple particles to the detection chamber.

In another preferred embodiment of the invention, displacing some of the multiple particles comprises reducing a volume of the detection chamber which, in turn, may comprise reducing a distance between first and second walls of the chamber.

In a further embodiment, the inventive method comprises positioning multiple particles of a sample within a detection chamber, displacing some of the multiple particles from the detection chamber so that only a proper subset of the multiple particles remains, optically detecting particles of the subset of multiple particles, and determining the presence or a target particle among the subset of particles.

In another embodiment, the inventive method comprises positioning a first multiple of particles of a sample within a detection chamber, reducing a volume of the detection chamber, optically detecting particles within the detection chamber, based on the detected particles, determining a value indicative of the number of particles present within the detection chamber, increasing a volume of the detection chamber, positioning a second multiple of particles of the sample within the detection chamber, reducing a volume of the detection chamber, and based on the detected particles, determining a value indicative of the number of particles present within the detection chamber.

In a further aspect, the invention relates to a device comprising a detection chamber configured to receive a sample comprising multiple particles, an actuator configured to displace some of the multiple particles from the detection chamber so that only a proper subset of the multiple particles remains, a detector configured to detect particles of the subset of particles, and a processor configured to determine, based on the detected particles, a value indicative of the number of particles of the proper subset of particles.

Preferably, the device is configured to operate the actuator to reintroduce at least some of the displaced multiple particles to the detection chamber and, subsequently, to displace some of the multiple particles from the detection chamber so that only a second proper subset of the multiple particles remains and the processor is configured to operate the detector to detect particles of the second proper subset and determine, based on the detected particles, a value indicative of the number of particles of the second proper subset of particles.

The device may further comprise a reservoir capable of receiving particles displaced from the detection chamber and from which particles can be reintroduced to the detection chamber.

In one embodiment, the processor may be configured to determine, based on the detected particles, the presence of a target particle among particles of the subset of particles.

BRIEF DESCRIPTION OF THE DRAWINGS

FIGS. 4A and 4B illustrate specific embodiments of an inventive assay device or an inventive assay system (A) as well as its mode of operation (B).

DETAILED DESCRIPTION OF THE INVENTION

Figure 1:
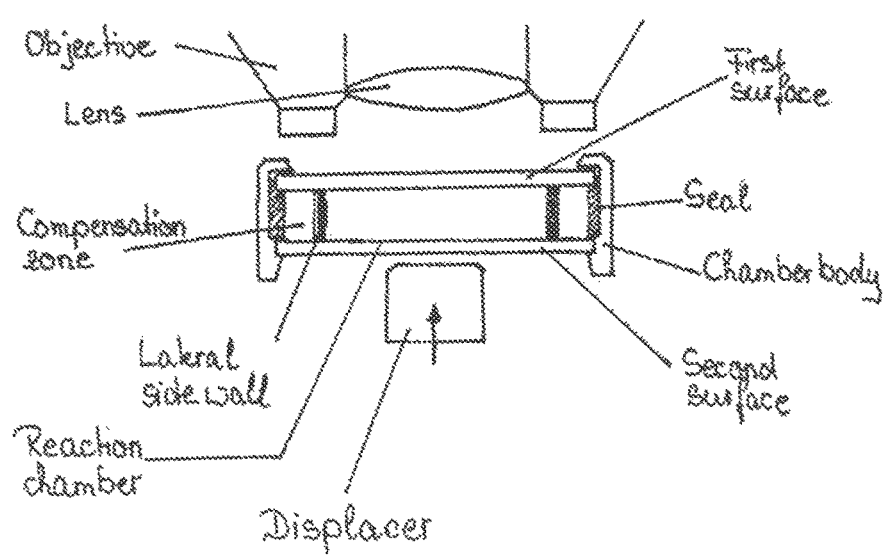
FIG. 1 is a schematic cross-sectional view of an inventive assay device comprising an optical detection system.

In a first aspect, the present invention relates to a device for the qualitative and/or quantitative detection of particles, comprising:

(a) a reaction chamber formed within a chamber body between a first surface and a second surface, wherein the second surface is located opposite to the first surface; and
(b) one or more displacers, wherein the distance between the first surface and the second surface is variable via the one or more displacers at least in one or more parts of the surface area of the first surface and/or the second surface.

Within the scope of the present invention, a "reaction chamber" (herein also referred to as "reaction space" or "detection chamber" or "chamber") denotes the space formed within a chamber body between a first surface and a second surface. The reaction chamber may be of any basic shape, for example circular, elliptical, quadratic, or rectangular. Preferred reaction chambers of the invention have a cuboid or cylindrical three-dimensional shape. Particularly preferred are reaction chambers being configured as (capillary) channels. Optionally, the reaction chamber may comprise tapering parts. For example, the reaction chamber may taper from the central area to either one or both terminal regions. The reaction chamber is laterally limited by sidewalls. The second surface is located opposite or substantially opposite to the first surface. Preferably, the first and second surfaces are arranged in parallel or substantially parallel to each other.

The distance between the first surface and the second surface is defined as the distance between the side of the first surface of the device facing the reaction chamber and the side of the second surface facing the reaction chamber and is also referred to as thickness of the reaction chamber. According to the present invention, the thickness of the reaction chamber is usually at most 1 cm, preferably at most 5 mm, particularly preferably at most 3 mm and most preferably at most 1 mm.

In some embodiments of the invention the reaction chamber is designed as a capillary gap, which can be filled by means of capillary forces acting between the first and second surfaces. Usually, a capillary gap has a thickness of at most 1 mm, preferably of at most 750 µm and particularly preferably of at most 500 µm. In preferred embodiments of the invention, the capillary gap has a thickness of 300 µm, with a thickness of 200 µm being more preferred, and a thickness of 150 µm being particularly preferred.

In assay devices according to the present invention the distance between the first surface and the second surface is variable. In preferred embodiments, the distance is variable in a range of 0 mm to 1 mm. Further preferred lower limits for the distance between the first surface and the second surface are in the range of 50 µm to 200 µm. Further preferred upper limits are in the range of 0.3 mm to 0.5 mm.

The term "displacer" or "actuator", as used herein, denotes a means that is suitable to displace a solution within the reaction chamber or in at least in one or more parts of the reaction chamber of an inventive device upon a variation of the distance between the first surface and the second surface in at least in one or more parts of the surface area of the first surface and/or the second surface. In other words, a displacer of the invention may also be defined as a means allowing the vertical movement of the first surface and/or the second surface, or at least one or more parts thereof, relative to each other. The term "at least in one or more parts of the surface area", as used herein, is to be understood that a variation of the distance between the first surface and the second surface via a displacer may not necessarily occur over the entire surface area of the first surface and/or the second surface (i.e. either one or both of said surfaces as a whole are vertically moved relative to each other) but may also be locally restricted to at least one part of the surface area of either one or both of said surfaces (i.e. only these one or more parts of the surface area(s) of the respective surface (s) is/are moved vertically relative to each other, whereas the distance in the remaining one or more parts of the surface area(s) of the respective surface(s) remains substantially constant). In preferred embodiments of the present invention, the distance between the first surface and/or the second surface is reduced, particularly preferably by applying pressure to at least a part of either one or both of said surfaces.

A displacer according to the invention may constitute an integral part of the first surface or the second surface (herein also referred to as "displacement structure") or may represent an independent, i.e. self-contained, entity (herein also designated "displacement body") located outside the reaction chamber. In case a displacer is provided as a displacement structure, i.e. an integral part of the first surface or the second surface, it may be designed as a convex entity extending to the inside of the reaction chamber. Such a convex entity may have any shape that is suitable for causing a displacement of a solution within the reaction chamber when performing the inventive method. Examples of such convex shapes include inter alia a dent, a ridge, a buckle, and a bulge, with the latter one being preferred. In accordance with its nature as an integral part of the first surface or the second surface such a displacement structure can be made of the same material as the remainder of the respective surface or at least a part thereof.

In other embodiments of the invention, a displacer constitutes an independent displacement body not integrated into the first surface or the second surface but located opposite to either one of said surfaces, wherein the displacer is located at the side of the respective surface facing away from the reaction chamber. In some embodiments, the displacer is located perpendicular to the respective surface of the reaction chamber. Such a displacement body may have any shape that is suitable, when applied in the invention, to cause a displacement of a solution within the reaction chamber. Examples of such displacement bodies include inter alia a human finger, a rod, a pin, a plunger, a spike, a pole, a tappet, and a stencil, with the latter two being particularly preferred.

Within the scope of the invention, the device may comprise one or more displacers, all of which either may be integral parts of the first surface and/or the second surface or may be displacement bodies. However, it may also be possible that an inventive device comprises at least one displacement body and at least one displacement structure integrated in one of said surfaces. In preferred embodiments of the invention, the device comprises two displacers. In other embodiments, the device comprises at least three, at least four, at least eight or at least 12 displacers.

All of the displacers of an inventive device may be integrated in and/or located opposite to either of the first surface or the second surface. Alternatively, it is also possible that a device comprises at least two displacers that are integrated in and/or located to both of said surfaces. In preferred embodiments of the invention, the device comprises at least two displacers, which are solely of the displacement body type located opposite to the first surface and/or the second surface. In a particularly preferred embodiment, the device comprises two displacers, wherein both displacers are located opposite either to the first surface or to the second surface. In another particularly preferred embodiment, the device comprises two displacers as well, but one displacer is located opposite to the first surface, and the other displacer is located opposite to the second surface.

In a third particular preferred embodiment, the two displacers located opposite to different surfaces are also located opposite relative to each other.

The displacers can be made of any material that is suitable to cause an at least partial displacement of a solution within the reaction chamber, preferably by applying pressure to the first surface and/or the second surface giving rise to a variation (i.e. an reduction) of the distance between said surfaces. Typically, the displacer(s) is/are made of an amorphous material. The term "amorphous material", as used herein, refers to a solid in which there is no long-range order of the positions of the atoms, i.e. a non-crystalline material. Examples of such amorphous materials include inter alia ceramic materials such as aluminum oxide ceramics, glasses such as borofloat glasses, silicone, and synthetic polymers such as polystyrene or polytetrafluorethylene (Teflon™). Optionally, the amorphous material may also be optically transparent, i.e. a light-permeable. Examples of suitable transparent materials include inter alia glasses or glass-like materials such as window glass, borofloat glasses, quartz glasses, topaz glass, or sapphire glass, as well as synthetic polymers such as polymethylmethacrylate, polycarbonate, polycarbonate, polystyrene, or acryl. In case the inventive device comprises more than one displacer, all of them can be made of the same material or at least one of them can be made of a different material.

In preferred embodiments of the invention, at least one of the one or more displacers is made of an elastically deformable material, i.e. a material that after having been deformed at least substantially restores its original shape independently without any further external manipulation. Optionally, such elastically deformable materials according to the invention are further preferred to be biologically/chemically inert (i.e. to have no or a very low reactivity towards chemical and/or biological reagents), optically transparent and/or not autofluorescent. Examples of such materials include inter alia silicone elastomers, polyurethanes, triethyl phosphates, acrylics, and acrylates, with silicone elastomers being particularly preferred. Silicon elastomers are primarily composed of cross-linked silicone polymers. These polymers have a —Si—O— backbone of the chemical formula $[R_2SiO]_n$, where R represents organic side groups such as methyl, ethyl, phenyl or the like, which can be used to crosslink two or more polymers. By varying the —Si—O— chain lengths, side groups, and crosslinking, silicones can be synthesized with a wide variety of properties and compositions. They can vary in consistency from liquid to gel to rubber to hard plastic. The most common type is linear polydimethylsiloxane. Another group of silicone materials is based on silicone resins, which are formed by branched and cage-like oligosiloxanes. In a particularly preferred embodiment, the elastically deformable material is selected from the group consisting of a silicone rubber and a silicone oil. Further suitable materials include natural rubber, that is the rubber extracted of the Para rubber tree (*Hevea brasiliensis*), as well as further composition rubbers (commonly also referred to as synthetic rubbers) that can be made by polymerization of a variety of monomers including, e.g., isoprene (2-methyl-1,3-butadiene), 2-chloro-1,3-butadiene, and methyl-propene with a small percentage of isoprene for cross-linking. Examples of suitable composition rubbers include inter alia styrene-butadiene rubber, acrylonitrile-butadiene rubber, urethane rubber, polyester rubber, chloroprene rubber, butyl rubber, epichlorohydrin rubber, and phosphazene rubber.

In some embodiments of the invention, the first surface and/or the second surface comprise(s) a surface area where detection takes place, i.e. a detection area (herein also referred to as "detection zone"). That is the qualitative and/or quantitative detection of the one or more species of particles to be analyzed is restricted to a distinct surface area of either one or both of said surfaces, for example it may be possible that detection and/or enumeration of the particles will take place only in the central section of the first surface and/or the second surface, probably due to spatial constraints of the detection system used. Preferably, the volume of the section of the reaction chamber that is limited by the detection area(s) of the first surface and/or the second surface is known to allow for quantitative analyses. In some embodiments of the invention, the "detection area" between the first surface and the second surface is designed as a capillary gap that is preferably located in the central part of the reaction chamber, wherein the distance between said surfaces in this area may optionally be smaller than the distance in the remaining parts of the reaction chamber.

In other embodiments of the invention, at least one or more parts of the first surface and/or the second surface is/are elastically deformable. That is, at least one or more parts of the respective surface(s) is/are made of an elastically deformable material, for example an elastic membrane, as described above in connection with the one or more displacers. A particularly preferred elastic membrane according to the invention is made of silicone rubber. Thus, in one embodiment the entire surface area of the first surface and/or the second surface can be made of an elastically deformable material. In one embodiment of the invention, the whole reaction chamber is elastically deformable, that is, the first surface, the second surface, and the lateral side walls. Preferably, the at least one or more elastically deformable parts of the first surface and/or the second surface are located opposite to the one or more displacers. Accordingly, all surface areas of an inventive device located opposite of a displacer may be elastically deformable. However, it is also possible that at least one such surface area located opposite to a displacer is not elastically deformable. In one preferred embodiment of the invention, the at least one or more elastically deformable parts of the first surface and/or the second surface are different from the respective surface area(s) where detection take(s) place.

According to the present invention, the first surface and the second surface can be made of the same material or of different materials. Furthermore, it is also possible that the first surface and/or the second surface comprise(s) surface areas made of different materials as the remainder of the respective surface area. For example, one surface area of the first surface and/or the second surface, such as a central, optionally rectangular, surface area (i.e. a "window"), is made of a transparent material, whereas the remainder of the respective surface area (i.e. the "border") is made of a non-transparent material. Preferably, such a "window" of transparent material is located within the surface region where detection takes place.

At least a part of the first surface and/or the second surface of device according to the invention may be made of an amorphous material. The term "amorphous material", as used herein, refers to a solid in which there is no long-range order of the positions of the atoms, i.e. a non-crystalline material. Examples of such amorphous materials include inter alia ceramic materials such as aluminum oxide ceramics, glasses such as borofloat glasses, silicone, and synthetic polymers such as polystyrene or polytetrafluorethylene (Teflon™).

In preferred embodiments of the invention, at least a part of the first surface and/or the second surface is/are made of a transparent material, i.e. a light-permeable material. Examples of suitable transparent materials include inter alia glasses or glass-like materials such as window glass, borofloat glasses, quartz glasses, topaz glass, or sapphire glass, as well as synthetic polymers such as polymethyl-methacrylate, polycarbonate, polycarbonate, polystyrene, or acryl.

A device according to the present invention may further comprise a microarray (herein also referred to as "array" or "array element") being disposed on the first surface and/or the second surface of the reaction chamber. As used herein, a "microarray" denotes a defined spatial arrangement (layout) of capture molecules (e.g., one or more species of probe molecules or a substance library) on a support (also referred to as substrate), wherein the position of each molecule within the microarray is determined separately. Preferably, the microarray comprises defined sites or predetermined regions, i.e. so-called array elements or spots, which may be arranged in a particular pattern, wherein each array element preferably comprises only one species of capture molecules. The arrangement of the capture molecules on the support can be generated by means of covalent or non-covalent interactions. Suitable substrates for microarrays include inter alia microscope slides, wafers or ceramic materials. However, the capture molecules may also be directly immobilized on the first surface and/or the second surface.

The device according to the present invention may further comprise one or more means, which, when the distance between the first surface and the second surface is reduced, allow keeping the volume of the reaction chamber essentially constant. That is, compensation zones (or "reservoirs") are provided to which any liquid material being present in the reaction chamber between the first surface and the second surface can be displaced when the distance between said surfaces is reduced. The term "essentially constant", as used herein, is to be understood that upon a reduction of the distance between the first surface and the second surface the volume of the reaction chamber in the "compressed" state has not to be exactly the same as its original volume in the "uncompressed" state. Preferably, the volume of the reaction chamber in the "compressed" state is at least 90% of the volume in the "uncompressed" state, particularly preferable at least 95%. In some embodiments of the invention, any reagents required for performing the inventive methods such as agents comprising detectable moieties (i.e. labels) or buffers are provided in the compensation zones or reservoirs, preferably in dry form (e.g. in lyophilized form as powders, granules or pellets).

Preferably, this is accomplished by providing a reaction chamber laterally delimited by sidewalls made of an elastic material. According to the present invention, one or more lateral sidewalls can be made of an elastic material. A particularly preferred elastic material is silicone rubber.

In another embodiment, the inventive device further comprises a chamber body. The term "chamber body", as used herein, is understood to denote the solid body surrounding the reaction chamber, which is formed by the first surface, the second surface, and the lateral sidewalls.

The first surface, the second surface, and/or one or more of the lateral sidewalls may be integral part(s) of the chamber body. That is, the respective surface(s) being an integral part of the chamber body is/are made of the same material as the chamber body. Alternatively, one or more of the first surface, the second surface, and/or one or more lateral sidewalls, respectively, may be made of another material than the chamber body. Within the scope of the present invention, it is thus possible that all four surfaces defining the reaction chamber are made of the same material, that two or three surfaces are made of the same material, whereas the remaining surface(s) is (are) made of different material(s), or that each surface is made of different materials.

The first surface and/or the second surfaces and/or one or more lateral sidewalls delimiting the reaction chamber may further comprise one or more openings, which may be lockable and/or scalable, and which may be used for the direct introduction of a sample to be analyzed as well as any additional reagents, detection agents or the like that may optionally also be required for performing the method of the invention. Alternatively, such openings may also be used for the attachment of any additional (supplementary) modules of the device that have not been designed as integral parts of the chamber body, such as inter alia filling units, processing units, temperature control units, specific (i.e. complex) detection units, and waste containers. A connection between the reaction chamber and one or more of such additional modules may be achieved inter alia by using one or more rigid or flexible tubes, nozzles, cannulae, needles or the like, which may be attached to the reaction chamber and the additional module, respectively, inter alia by means of press-fit (also referred to as "Luer system") or twist-on fitting (also referred to as "Luer-lock system"), with the latter one being preferred. Both systems are well established in the art and commercially available.

The chamber body is preferably made at least in part of an amorphous material, in particular of a transparent material. Suitable materials include inter alia glass, synthetic materials such as Macrolon™, nylon, polymethylmethacrylate, Tetlon™, and metals such as high-grade steel, aluminum, and brass. In some embodiments, the chamber body is made of electrically conductive material, which is preferably selected from the group consisting of polyamide with 5 to 30% carbon fibers, polycarbonate with 5 to 30% carbon fibers, polyamide with 2 to 20% stainless steel fibers, and polyphenylensulfide with 5 to 40% carbon fibers.

The devices according to the present invention are typically operated as a single (i.e. individual) entity. However, it may also be possible to assemble two or more such devices to a multipart system comprising separate reaction chambers in order to perform multiple assays of one sample in parallel wherein a device as described above corresponds to a part or unit or entity of the multipart system. Thus, in a further aspect, the present invention relates to a system, comprising at least two parts, wherein each of the at least two parts comprises a reaction chamber formed within a chamber body between a first surface and a second surface, wherein the second surface is located opposite to the first surface; and one or more displacers, wherein the distance between the first surface and the second surface is variable via the one or more displacers at least in one or more parts of the surface area of the first surface and/or the second surface. The reaction chambers of the at least two parts of the system may be in communication with each other.

The term "in communication with each other", as used herein, denotes any interconnection between the individual reaction chambers, either directly or indirectly via an additional means such as a common sample introduction passage, filling unit, processing unit or the like. However, as used herein, the term does not necessarily mean that, after introducing a sample, the reaction chambers are in permanent fluid communication with each other.

In a preferred embodiment, the system further comprises a sample introduction passage which is in communication with each of the reaction chambers of the at least two devices. The sample introduction passage (herein also referred to as "sample loading zone" or "sample area") may comprise one or more lockable and/or scalable openings, as described above, for introducing the sample to be analyzed. The sample introduction passage may be configured as a chamber from which the respective reaction chambers branch off. The openings connecting the sample introduction passage and the reaction chambers may be lockable and/or sealable as well. In particular, it is preferable to prevent, after introducing a sample into the separate reaction chambers of such a multipart system, a backflow of liquid from a reaction chamber into the common sample introduction passage which would result in a mixing of sample solutions from different reaction chambers comprising variable reagents (such as capture molecules, labels and the like) and thus an interference with proper detection of the multiple individual assays to be performed in parallel.

Thus, in a further preferred embodiment of the invention, the system further comprises one or more means that allow for a transient fluid communication between the at least two reaction chambers. It is particular preferred to allow only for a unidirectional fluid communication from the sample introduction passage to the separate reaction chambers but not backwards. This may preferably be achieved by the provision of one-way valves at the connections between the sample introduction passage and the reaction chambers which prevent backflow of the sample from the reaction chambers.

In preferred embodiments of the invention, the device further comprises a detection system connected to the reaction chamber. Preferably, the detection system is positioned opposite to the first surface and/or the second surface, optionally in a particular surface region where detection takes place.

The selection of a suitable detection system depends on several parameters such as the optional presence of additional agents (e.g. dyes or labels) used for detection or the kind of particles to be detected. Various optical and non-optical detection systems are well established in the art. A general description of detection systems that can be used with the invention can be found, e.g. in Lottspeich, F., and Zorbas H. (1998) *Bioanalylik*, Spektrum Akademischer Verlag, Heidelberg/Berlin, Germany, in particular in chapters 23.3 and 23.4.

In a preferred embodiment of the invention, the detection system is an optical detection system. In general, performing the method according to the present invention does not require the use of sophisticated instrumentation but rather involves simple detection systems, preferably based on the measurement of parameters such as fluorescence, optical absorption, resonance transfer, and the like.

Particularly preferred detection systems according to the invention are based on apsorption measurements such as turbidimetry and nephelometry (see for review. e.g., Tiffany, O. (1986) *Fluorometry, nephelometry, and turbidinetry*, in: Tietz, N. O. (ed.). *Textbook of Clinical Chemistry*, WB Saunders Co., Philadelphia, Pa., pp. 78-97), which may be achieved with photometric devices established in the art. Both methods allow the determination of the "cloudiness" or turbidity in a solution based upon measurement of the effect of this turbidity upon the transmission or scattering of light, respectively. Turbidity in a liquid is caused by the presence of particles suspended therein. If a beam of light is passed through a turbid sample, its intensity is reduced. Turbidimetry refers to the measurement of unscattered light, i.e. light that is transmitted through a turbid solution of particles that can be performed using a standard photometer. Nephelometry, on the other hand, is the measurement of (side) scattered light. This technique requires a special instrument, where the detector is set at an angle to the incident light beam.

Also preferred for use in the present invention are detection systems based on the comparison of the fluorescence intensities of spectrally excited particles labeled with fluorophores. Fluorescence is the capacity of particular molecules to emit their own light when excited by light of a particular wavelength resulting in a characteristic absorption and emission behavior. In particular, quantitative detection of fluorescence signals is performed by means of modified methods of fluorescence microscopy (for review see, e.g., Lichtman, J. W., and Conchello, J. A. (2005) *Nature Methods* 2, 910-919; Zimmermann, T. (2005) *Adv. Biochem. Eng. Biotechnol.* 95. 245-265). Thereby, the signals resulting from light absorption and light emission, respectively, are separated by one or more filters and/or dichroites and imaged on suitable detectors. Data analysis is performed by means of digital image processing.

Image processing may be achieved with several software packages well known in the art (such as Mathematica Digital image Processing, EIKONA, or Image-PRO). Since the present invention is intended to be performed without any removal and/or replacement of solutions from the reaction chamber (that is, detection is performed in the presence of any unbound labels giving rise to an unspecific signal background), it is preferred to use an image processing software allowing for an efficient and accurate correction of background noise. Particularly preferably, detection of specific signals is not only achieved by measuring differences in signal intensities but also by concomitantly taking into account additional parameters such as the "shape" of the signal to be detected, which is again determined by the shape of the particles to be detected. For example, a circular particle such as a cell of circular shape that is labeled with a fluorescent antibody will result in a "circular signal" in the image recorded during optical detection. A preferred software suitable for such purposes is the Iconoclust software (Clondiag Chip Technologies GmbH, Jena, Germany).

Another optical detection system that may be used in the present invention is confocal fluorescence microscopy, wherein the object is illuminated in the focal plane of the lens via a point light source. Importantly, the point light source, object and point light detector are located on optically conjugated planes. Examples of such confocal systems are described in detail, e.g., in Diaspro, A. (2002) *Confocal and 2-photon-microscopy: Foundations. Applications and Advances*, Wiley-Liss, Hobroken, N.J. The fluorescence-optical system of the present invention is particularly preferred to represent a fluorescence microscope without an autofocus, for example a fluorescence microscope having a fixed focus.

In alternative devices according to the present invention means for performing an electrochemical detection of the analytes are provided, for example by measuring the alteration of redox potentials via electrodes connected to the first surface and/or the second surface (see, e.g., Zhu, X. et al. (2004) *Lab Chip*. 4, 581-587) or by cyclic voltometry (see, e.g., Liu, J. et al. (2005) *Anal. Chem.* 77, 2756-2761; and Wang, J. (2003) *Anal. Chem.* 75, 3941-3945). Furthermore, it is also possible to provide means for performing an electric detection, for example by impedance measurement (see, e.g., Radke. S. M. et al. (2005) *Biosens. Bioelectron.* 20, 1662-1667).

Typically, the devices and systems according to the present invention are self-contained. That is, they do not necessarily require removal and/or replacement of the sample and/or any other reagents in the reaction chamber while performing an assay. Thus, preferred embodiments of devices and systems of the invention only comprise a sample inlet port but no outlet port.

In a further aspect, the present invention provides a method for the qualitative and/or quantitative detection of particles, comprising:
(a) positioning a sample supposed to comprise one or more species of particles to be detected in a reaction chamber;
(b) displacing at least a part of the sample within the reaction chamber via the one or more displacers; and
(c) detecting/determining a value indicative for the presence and/or number of one or more species of particles.

In preferred embodiments of the invention, "positioning a sample in a reaction chamber" comprises introducing said sample into the reaction chamber of an inventive device or system as described above.

In a further particular preferred embodiment of the invention, the method comprises:
(a) positioning a sample comprising multiple particles in a reaction chamber;
(b) displacing a subset of said multiple particles within the reaction chamber via the one or more displacers; and
(c) determining one or more values indicative for the number of the subset of particles displaced in step (b).

Optionally, the method further comprises:
(d) calculating the total number of the multiple particles in the reaction chamber from the one or more values obtained in step (c).

In some embodiments of the invention, the quantitative detection/determination in step (c) comprises the counting of one or more species of particles in a sample, for example the enumeration of cells in a biological sample.

The term "sample", as used herein, refers to a liquid which is to be analyzed by using a device according to the present invention, and which is supposed to comprise one or more species of particles to be detected. Preferably, the sample to be analyzed is a biological sample. Examples of liquid samples that can be analyzed using the invention include inter alia organic and inorganic chemical solutions, drinking water, sewage, human and non-human body fluids such as whole blood, plasma, serum, urine, sputum, salvia or cerebrospinal fluid, cellular extracts from animals, plants or tissue cultures, prokaryotic and eukaryotic cell suspensions, phage preparations and the like. The sample may further comprise one or more additional agents such as diluents, solvents or buffers that may result from an optional purification and/or processing of the sample prior to its introduction (positioning) into the reaction chamber.

The sample to be analyzed may comprise one or more species of particles to be detected when performing the present invention. The term "particle", as used herein, denotes any entity having a specific binding behavior and/or a characteristic reactivity, which enables its detection by performing the method of the invention. Accordingly, the term "particle" is not only to be construed in a literal sense as referring to "true" particles such as cells or viruses but also to be understood as comprising molecules to be detected, in particular (biological) macromolecules such as nucleic acid, proteins, lipids, and carbohydrates as well as analogs and/or mixtures thereof having binding affinity to any (synthetic) particles present in or added to a sample to be analyzed.

The term "species", as used herein in connection with the term particles, refers to a particular type of particle, i.e. a specific type of cells or a specific phage, for example. Accordingly, the term "one or more species" denotes one or more different types of particles such as one or more different cell types.

"True" particles according to the present invention include naturally occurring as well as synthetic particles. Examples of such naturally occurring particles include inter alia prokaryotic cells (e.g. bacterial cells such as *Escherichia coli* or *Bacillus subtilis*), eukaryotic cells (e.g. yeast cells such as *Saccharomyces cerevisiae*, insect cells such as Sf9 or High 5 cells, immortalized cell lines such as HeLa or Cos cells, and primary cells such as mammalian blood cells) or viruses (e.g. phage particles such as M13 or T7 phage). Examples of synthetic particle include inter alia (paramagnetic) polystyrene beads and latex beads, optionally be coated with one or more species or molecules to be detected by the present invention, in particular one or more species of (biological) macromolecules such as nucleic acids, proteins, lipids or carbohydrates.

The sample to be analyzed may be introduced directly into the reaction chamber via one or more openings, which may be lockable and/or scalable, being present in the first surface, the second surface and/or one or more lateral sidewalls. The sample may be transferred, optionally along with additional reagents, into the reaction chamber by using a suitable pressure-generating means, for example, a pipette, a syringe or an automated unit, which may be, for example, a functional unit of a processing apparatus. Alternatively, the sample may also be introduced into the reaction chamber by capillary force without any external manipulation, for example by placing the sample immediately adjacent to one of the openings being present in any of the surfaces defining the reaction chamber.

In a specific embodiment of the inventive method, the sample is introduced into the reaction chamber by means of negative pressure caused by operating the one or more displacers. In this embodiment, initially, i.e. before adding the sample, the distance between the first surface and the second surface in at least in one or more parts of the reaction chamber, or in other words, in at least in one or more pans of the surface area of the first surface and/or the second surface is reduced by applying pressure towards the first and/or second surface via the one or more displacers. Preferably, the distance is reduced to a value of zero or almost zero. Then, said reduced distance is re-increased, preferably to the initial value, by resetting the displacer (i.e. by moving it in backwards direction) thus causing a negative pressure within the reaction chamber which, in turn, allows for introducing the sample into the reaction chamber.

The method of the present invention is intended to be performed without the requirement to remove and/or replace the sample and/or any other reagents in the reaction chamber while performing the method. In particular, it is an advantage of the inventive method that no washing or rinsing steps that would require such removal/replacement are necessary, for example in order to improve the signal-to-noise ratio of the detection method used. However, some applications may require the introduction of additional reagents into the reaction chamber such as one or more agents comprising any labels in order to allow further detection of the particles of interest. Such additional solutions may also be directly introduced into the reaction chamber, as described above, either before introducing the sample or concomitantly with the sample or after the sample has been introduced into the reaction chamber. In preferred embodiments, the additional reagents are provided within the device (e.g., in the compensation zones) before adding the sample, particularly in lyophilized/dry form such as powders, granules or pellets.

Alternatively, introducing the sample to be analyzed, and optionally of further reagents, may also be possible in an indirect manner by means of one or more filling units.

Within the scope of the present invention, a "filling unit" denotes a means for filling the reaction chamber which may be an integrated part of the device of the invention or it may be designed as a separate part that can be attached to the reaction chamber for filling the same and detached after use. Any container that is capable of holding a liquid sample to be analyzed in the invention and that can be (reversibly) connected to the reaction chamber may be used as filling unit. A connection between reaction chamber and filling unit may be achieved inter alia by means such as tubes, nozzles, cannulae, needles or the like, as already described above. A given sample can be introduced into one or more lockable and/or scalable openings of the filling unit in the same way as described above for the direct introduction into the reaction chamber.

In special embodiments, one or more cannulae are used for connecting a filling unit to the reaction chamber of the device. The cannulae used penetrate the lock and/or seal of one or more of the openings comprised in the reaction chamber. Preferred cannulae used in the invention are made of high-grade steel or of synthetic polymers and usually have a diameter of 0.05 mm to 2 mm. Preferably, two cannulae are arranged in such a way that one is used for introducing the sample into the reaction chamber and the other one for taking up excess gaseous material and/or surplus liquids from the reaction chamber (for a detailed description see also the International Patent Application WO 01/02094, whose relevant contents are herewith explicitly referred to).

The filling unit may comprise an integrated or a detachable separate waste container, which serves for taking up surplus media from the reaction chamber. Optionally, the waste container comprises with a further gaseous, liquid, or solid filler medium such as inter alia cellulose, filter materials, and silica gels, which binds the surplus substances reversibly or irreversibly. Furthermore, the waste container may comprise one or more air vents or may be provided with a vacuum in its interior for improving the transfer of surplus material to the waste container.

The filling unit may further comprise mechanical means ensuring that it accurately fits the respective attachment site of the reaction chamber, i.e. that the filling unit is exactly positioned relative to the reaction chamber to allow connecting the filling unit to the reaction chamber via one or more cannulae, nozzles or the like at preferred sites such as the lockable and/or scalable openings. Examples of such mechanical means include inter alia specifically designed snap fits or spring locks. Preferably, the mechanical means allow detaching the filling unit after introducing the sample and any optional reagents into the reaction chamber.

One advantage of the present invention refers to the fact that sample volumes of less than 10 µl can be analyzed. Typically, sample volumes are in a range of 1 to 1.000 µl, preferably in a range of 1 to 100 µl, more preferably in a range of 1 to 25 µl, and most preferably in a range of 1 to 5 µl.

The samples to be analyzed can be introduced into the reaction chamber without any further purification, since the inventive device and method are specifically designed to allow the qualitative and/or quantitative detection of any particles in a given sample without the requirement to perform washing and rinsing steps. However, in some cases it might be preferable to purify the sample, at least partially, for example in order to remove any crude contaminations that would otherwise interfere with further detection. Such (partial) purification of the sample can be accomplished in different ways, for example by filtration of the sample before introducing it into the reaction chamber.

Furthermore, it may be required to dilute a sample to be analyzed due to a comparably high viscosity that would otherwise interfere with the diffusion of the sample throughout the reaction chamber of the inventive device. Dilution of the sample can be easily achieved by adding a diluent to the sample. Examples of suitable diluents include inter alia water, organic and inorganic solvents, phosphate-buffered saline and the like. The diluent may be added before introducing of the sample into the device or may be directly added into the filling unit and/or the reaction chamber, as described above.

After the sample, and optionally any additional reagents, have been introduced into the reaction chamber or have been transferred from the one or more filling units into the reaction chamber, the sample may optionally be incubated in the reaction chamber for a given period of time to allow proper diffusion throughout the reaction space. Typically, the incubation period is in the range of 1 s to 30 min, preferably in the range of 10 s to 15 min, and particularly preferably in the range of 30 s to 10 min.

In some preferred embodiments, the method according to the present invention further comprises introducing one or more agents each comprising one or more detectable moieties into the reaction chamber of the device before performing step (b). That is, the agents comprising one or more detectable moieties may be introduced into the reaction chamber before introducing the sample, concomitantly with the sample, or after the sample has been introduced either directly or via a filling unit, as described above.

The term "agent comprising one or more detectable moieties", as used herein, refers to any compound that comprises one or more appropriate chemical substances or enzymes (i.e. one or more "moieties"), which directly or indirectly generate a detectable compound or signal in a chemical, physical or enzymatic reaction. Such an agent may thus be necessary for or will facilitate detection of one or more species of particles of interest by being capable of forming interactions with said particles. As used herein, the term is to be understood to include both detectable markers as such (also referred to as "labels") as well as any compounds coupled to one or more such detectable markers.

In preferred embodiments, the one or more agents are selected from the group consisting of nucleic acids, peptides, protein domains, proteins, carbohydrates, low molecular weight chemical compounds, and analogs and/or mixtures thereof.

Examples of nucleic acids that can be used as in the present invention include naturally occurring nucleic acids such as deoxyribonucleic acid (DNA) or ribonucleic acid (RNA) as well as nucleic acid analogs such as inter alia peptide nucleic acids (PNA) or locked nucleic acids (LNA). Specific examples of naturally occurring nucleic acids include DNA sequences such as genomic DNA or cDNA molecules as well as RNA sequences such as hnRNA or mRNA molecules or the reverse complement nucleic acid sequences thereof. Such nucleic acids can be of any length and can be either single-stranded or double-stranded molecules, with single-stranded molecules being preferred. Typically, such nucleic acids used in the invention are 10 to 1000 bases in length, preferably of 15 to 500 bases, more preferably 20 to 100 bases and particularly preferably of 20 to 40 bases.

Peptides, protein domains or proteins that can be used as agents according to the present invention comprise naturally occurring as well as artificially designed molecules, for example by means of recombinant DNA technology or via chemical synthesis. Methods for the design and preparation of such proteinaceous molecules are well established in the art (see, for example, Sambrook, J. et al. (1989) *Molecular Cloning: A Laboratory Manual*, 2nd ed., Cold Spring Harbor Laboratory Press, Cold Spring Harbor, N.Y.). Typically, peptide agents of the invention are 2 to 200 amino acids in length, preferably 2 to 100 amino acids, more preferably of 5 to 50 amino acids, and particularly preferably of 10 to 25 amino acids.

The term "protein domain", as used herein, refers to a part of a polypeptide sequence that is defined with regard to the specific function it exhibits, such as ligand binding or catalytic activity. Preferred examples of such protein domains are inter alia Fab-fragments of antibodies, the ligand-binding domains of cellular receptors such as G-protein coupled receptors, receptor tyrosine kinases or nuclear receptors, and the carbohydrate-binding domain of lectins.

Examples of carbohydrates that can be used as agents in the present invention include monosaccharides such as glucose or fructose, disaccharides such as lactose or sucrose, as well as oligosaccharides and polysaccharides such as starch, with monosaccharides being preferred.

The term "low molecular weight chemical compound", as used herein, denotes an molecule, preferably an organic molecule, comprising at least two carbon atoms, but preferably not more than seven rotatable carbon bonds, having a molecular weight in the range between 100 and 2.000 Dalton, preferably between 100 and 1.000 Dalton, and optionally including one or two metal atoms. Examples of such molecules include inter alia imidazoles, indoles, isoxazoles, oxazoles, pyridines, pyrimidines, and thiazoles.

Detectable markers or labels that may be used according to the invention include any compound, which directly or indirectly generates a detectable compound or signal in a chemical, physical or enzymatic reaction. Preferably, the labels can be selected inter alia from enzyme labels, colored labels, fluorescent labels, chromogenic labels, luminescent labels, radioactive labels, haptens, biotin, metal complexes, metals, and colloidal gold, with fluorescent labels being particularly preferred. All these types of labels are well established in the art. A preferred example of a physical reaction that is mediated by such labels is the emission of fluorescence or phosphorescence upon irradiation or excitation or the emission of X-rays when using a radioactive label. Alkaline phosphatase, horseradish peroxidase, β-galactosidase and β-lactamase are examples of enzyme labels, which catalyze the formation of chromogenic reaction products, and which may be used in the invention. A preferred enzyme label is horseradish peroxidase, especially along with a substrate selected from the group consisting of 3-amino-9-ethylcarbazole, 4-chloro-1-naphthol, 3,3'-diaminobenzidine, and 3,3',5,5'-tetramethyl-benzidine, with the latter one being particularly preferred.

In preferred embodiments of the inventions, the one or more agents comprising one, or more detectable moieties are directly coupled to one or more species of particles to be detected, wherein it is to be noted that in the invention such coupling will typically not occur to the particles "as a whole" but to one or more species of particular molecules, preferably macromolecules such as a nucleic acid or a protein, on the surface of said particles. Such a "surface molecule" may be a molecule naturally occurring on the surface of cell (e.g. a cell surface receptor such as a G-protein coupled receptor or a particular carbohydrate moiety) or may be artificially coated to the surface of a particle, for example a nucleic acid molecule (also referred to as "capture molecule" or "molecular probe") coupled to a paramagnetic bead, for example via an biotin/avidin-linkage. The labeling reaction, i.e. the attachment of one or more detectable moieties to an agent of the invention, may be performed outside the inventive device, i.e. before introducing the sample, or directly in the device, optionally in the filling unit already described above. Labeling can be achieved by methods well known in the art (see, for example, Sambrook, J. et al., supra; and Lottspeich, F., and Zorbas H., supra).

Preferably, the one or more agents each comprising one or more detectable moieties have binding affinity for the particular "surface molecule" (or to the particle as such), to which they bind. Examples of such agents include inter alia antibodies as well as fragments thereof (e.g. Fab fragments), antibody-like molecules (e.g. anticalins), and DNA- or RNA-binding proteins as well as fragments thereof. Suitable antibodies or antibody fragments to be used in the invention include both primary antibodies which are raised against the particular analyte to be detected and secondary antibodies which are raised against immunoglobulin G of the animal species in which the primary antibody has been raised. Labeling is accomplished by coupling the agents to one or more detectable markers as described above.

In another preferred embodiment, one or more agents each comprising one or more detectable moieties and the "surface molecules" on the particles to be detected (or the particle as such) are allowed to form molecular interactions with each other, while being present in the reaction chamber. Finally, these molecular interactions are detected using an appropriate detection method.

After having introduced the sample, optionally along with any additional reagents, into the reaction chamber at least a part of the sample is displaced within the reaction chamber via the one or more displacers. The term "displaced", as used herein, is to be understood that the sample is moved within the reaction chamber by varying, preferably by reducing, the distance between the first surface and the second surface at least in one or more parts of the surface area of the first surface and/or the second surface via the one or more displacers, preferably by applying pressure to either one or both of said surfaces or at least one or more parts thereof. Accordingly, it is within the scope of the present invention either to vary the distance between the first surface and the second surface throughout the entire surface area of said surfaces or to vary the distance in only one part of the surface area such as at one terminal end of the reaction chamber or to vary the distance between the first surface and the second surface in at least two distinct parts of the surface area such as at both terminal ends of the reaction chamber.

A variation, preferably a reduction, of the distance between the first surface and the second surface is accomplished by vertically moving the first surface and/or the second surface relative to each other via the one or more displacers. The term "vertical movement", as used herein, denotes a movement of either one or both surfaces of the device perpendicular or substantially perpendicular to their respective surface areas, thus resulting in a variation of the distance between them. A variation of the distance between the first surface and the second surface can be achieved by vertically moving either one of the two surfaces in either direction or by moving both surfaces simultaneously in opposite directions. Accordingly, a reduction of the distance between the first surface and the second surface of the device can be achieved either by moving the first surface or at least one or more parts thereof towards the second surface, by moving the second surface or at least one or more parts thereof towards the first surface or by moving both surfaces or at least one or more respective parts thereof towards each other. Vice versa, an increase of the distance between the first surface and the second surface of the device can be achieved either by moving the first surface away from the second surface, by moving the second surface away from the first surface or by moving both surfaces away from each other. In particular, it is preferred to vary the distance between the first surface and the second surface by applying pressure and/or traction to either one or to both surfaces via said one or more displacers. Within the scope of the present invention, it is possible to apply pressure and/or traction concomitantly via all displacers present in a given device or via only at least one of them, whereas the other at least one displacers remain unused. For example, in a device of the invention comprising two displacers it is thus possible to apply pressure and/or traction to at least one part of the first surface and/or second surface concomitantly via both displacers or with only one of them in order to displace the sample within the reaction chamber.

Thus, in view of the different types of displacers defined above different modes concerning the variation, preferably reduction, of the distance between the first surface and the second surface (in the following the terms "first surface" and/or "second surface" are to be understood also to refer to at least in a part of the respective surface area) are conceivable, finally resulting in the displacement of at least a part of the sample within the reaction chamber.

First, in case a displacer constitutes an integral part of the first surface or the second surface (e.g. a displacement structure designed as a convex entity extending to the inside of the reaction chamber) for reducing the distance between said surfaces it is possible to move the respective surface comprising the displacement structure vertically towards the opposite surface, to move the opposite surface vertically towards the surface comprising the displacement structure, or to move both surfaces vertically relative towards each other. Optionally, the surface opposite of the "integrated" displacement structure also comprises a displacer at the respective (i.e. opposite) location, which may be integrated into the surface as well or may represent a displacement body, which will be operated as described below. Vertical movement of the respective surface(s) may either be achieved by one or more displacers of the displacement body type or by one or more additional means allowing the vertical movement of said surfaces. Such means may be integrated in or attached to the first surface and/or the second surface of the device or may comprise an independent entity. In some embodiments, the one or more means are selected from the group consisting of a human finger, a rod, a pin, a tappet, and a screw. If the device is integrated into an automated processing system, one or more means such as a stamp or a plunger connected to the reaction chamber may be used to apply pressure on the first surface and/or the second surface. Another means for applying pressure to the surfaces is to simply press them together in one's hand.

Second, in case a displacer is present in form of a displacement body for reducing the distance between said surfaces pressure may be applied to the respective surface, opposite to which the displacer is located, by moving said displacer towards the surface, which may optionally be made of elastically deformable material at least in this part of the surface area. The (elastically) deformation of the respective surface, i.e. a "movement" of the surface in vertical direction, via the displacer then results in a reduction of the distance between the first surface and the second surface. Optionally, a second displacer may be located opposite to the above-mentioned displacement body on the other "side" of the reaction chamber. This second displacer may either be a displacement structure integrated into the respective surface or may be another displacement body located opposite to it. Vertical movement of the second displacer occurs in reverse direction than that of the first displacer.

Reducing the distance between the first surface and the second surface of the reaction chamber at least in one or more parts of the surface area(s) results in a concomitant (spatially restricted) reduction of the reaction space at the respective sites at which the distance has been decreased. Accordingly, the sample to be analyzed becomes at least in part successively displaced from these sites and is "moved" within the reaction chamber, preferably to the compensation zones that allow keeping the volume of the reaction chamber essentially constant.

After having reduced the distance between at least one or more parts of the first surface and the second surface it is possible to immediately perform the detection, as will be described below.

The term "detecting/determining a value indicative for the presence and/or number of one or more species of particles", as used herein, refers to the determination of parameters such as electrical conductivity, redox potential, fluorescence intensity or bioluminescence that allow for qualitative and/or quantitative measurements of given particles in a sample. Within the scope of the present invention, only a single of these parameters may be determined but it is also possible to determine more than one parameter (e.g. electrical conductivity and the intensity of a fluorescence signal caused by a suitable label), either concomitantly or consecutively.

Preferably, the detection is performed in the part of the reaction chamber that is located between the detection area(s) of the first surface and/or the second surface, as described above. This part of the reaction chamber is also referred to as "detection zone". For quantitative measurements, i.e. the counting of particles, it is thus preferred to employ a device comprising a reaction chamber and a detection zone having known volumes, respectively.

However, at this stage of the method it is preferred to re-increase the distance between the at least one or more parts of the first surface and the second surface of the reaction chamber. It is particularly preferred to restore the original distance, i.e. the distance before the reduction, between the first surface and the second surface of the reaction chamber. This may be achieved by vertical movement of the at least one displacement structures and optionally also of the means allowing vertical movement of said surfaces, as described above, but in reverse direction, i.e. by discontinuing the application of pressure to the respective surfaces or surface areas. Optionally, the re-increase of the distance between the first surface and the second surface that has been reduced in a given surface area by applying pressure via a first displacer may be improved by reducing the distance in another surface area by applying pressure via a second displacer. Preferably, both displacers represent displacement bodies, which may be located opposite to the same surface, i.e. either the first surface or the second surface, or opposite to different surfaces. Re-increasing the distance between the two surfaces in the at least one or more surface areas of the first surface and/or the second surface results in a concomitant (optionally spatially restricted) increase in reaction space between the two surfaces. Furthermore, the sample having been displaced within the reaction space, preferably in the compensation zones provided, will now diffuse back in reverse direction. Thus, by using at least two displacers located at different site of the surface area of the first surface and/or the second surface that are operated in opposite directions, as described above, a continuous displacement, and thus also a mixing, of a sample within the reaction chamber may be achieved.

In a particularly preferred embodiment of the present invention, the subsequent reduction and re-increase of the distance between at least one or more parts of the first surface and the second surface is repeated at least twice. The extent to which the distance between at least one or more parts of the first surface and the second surface is reduced during two or more consecutive "compression/relaxation cycles" is preferably be the same. That is, the distance between the two surfaces in the compressed state of the device remains constant. However, it is also possible to vary the extent to which the distance between at least one or more parts of the first surface and the second surface is reduced during two or more consecutive "compression/relaxation cycles", for example by increasing the extent with an increasing number of cycles. Preferably, this subsequent reduction and re-increase of the distance is repeated until the sample is evenly distributed within the reaction chamber, i.e. equilibrium conditions have been established, which is essential for the reliability of quantitative analyses such as the counting of particles in a sample. Thus, when performing detection within a particular "detection zone" of the reaction chamber the determination of the mean value of repeated detection steps within this area will provide an accurate measure for the actual number of particles within the entire reaction chamber (provided that the volumes of the entire reaction chamber as well as that of the "detection zone" are known). The number of cycles of reduction and re-increase that can be performed is within the opinion of the practitioner. Typically, the number of cycles is in a range of 2 to 2000, preferably in a range of 10 to 1500, more preferably in a range of 50 to 1000 and particularly preferably in a range of 100 to 500.

According to the invention, the detection/determination of a value indicative for the presence and/or the number of the one or more species of the particles may be performed after each cycle of reducing and re-increasing of the distance between the first surface and the second surface of the reaction chamber, wherein the detection is preferably performed after said distance has been reduced. However, it is also possible to repeat the detection several times, for example after every second or every fifth reduction/re-increase cycle. Furthermore, it is possible to perform the detection only once after the completion of the last reduction/re-increase cycle. In a preferred embodiment, the detection is performed after each reduction/re-increase cycle. In other preferred embodiments of the invention, detection further comprises determining the mean value of the results obtained in the detection steps performed by then, as a measure allowing quantitative analyses being indicative for the total number of one or more species of particles being present in a sample. For example, after the second reduction/re-increase cycle the mean value of the results obtained after the first and the second reduction/re-increase cycle, respectively, is calculated; alter the third reduction/re-increase cycle the mean value of the results obtained after the first, the second, and the third reduction/re-increase cycle, respectively, is calculated, and so forth. The data obtained in one or more cycles of detection may be analyzed and mathematically processed using appropriate computer software known by persons skilled in the art in order to determine the presence and/or to calculate the number of particles.

Depending on the particular type of particle(s) to be detected as well as the nature of detectable markers used detection can be performed by various methods, all of them established in the art (see, for example, Ausubel. F. M. et al., supra; Coligan, J. E. et al. (2000) Current Protocols in Protein Sciences, Wiley & Sons, Hoboken, N.J.; and Lottspeich, F., and Zorbas H., supra).

Thus, performing the method according to the present invention generally does not require the use of sophisticated or bulky instrumentation but rather involves simple detection systems, preferably based on the measurement of parameters such as fluorescence, optical absorption, resonance transfer, and the like. Particularly preferred detection systems according to the invention are based on absorption measurements such as turbidimetry and nephelometry, as already described above, which may be achieved with photometric devices established in the art. Even though their simplicity these methods enable accurate determinations not only of the presence of a one or more given species of particles in a sample but also of their number (for review see, for example, Tietz, N. O. (ed.). Textbook of Clinical Chemistry. WB Saunders Co., Philadelphia. Pa., pp. 78-97)

Further particularly preferred detection systems are based "classical" methods for measuring a fluorescent signal such as epifluorescence or darkfield fluorescence microscopy (reviewed, e.g., in: Lakowiez, J. R. (1999) Principles of Fluorescence Spectroscopy, $2^{nd}$ ed., Plenum Publishing Corp. NY).

Further fluorescence detection methods that may also be used in the invention include inter alia total internal fluorescence microscopy (see, e.g., Axelrod, D. (1999) Surface fluorescence microscopy with evanescent illumination, in: Lacey, A. (ed.) Light Microscopy in Biology, Oxford University Press, New York, 399-423), fluorescence lifetime imaging microscopy (see, e.g., Dowling, K. et al. (1999) J. Mod. Optics 46, 199-209), fluorescence resonance energy transfer (see, e.g., Periasamy, A. (2001) J. Biomed. Optics 6, 287-291), bioluminescence resonance energy transfer (see, e.g., Wilson, T., and Hastings, J. W. (1998) Annu. Rev. Cell Dev. Biol. 14, 197-230), and fluorescence correlation spectroscopy (see, e.g., Hess, S. T. et al. (2002) Biochemistry 41, 697-705).

Alternatives for the above-mentioned detection systems include white light setups, as described, for example, in WO 00/12759, WO 00/25113, and WO 96/27025; confocal systems, as described, for example, in U.S. Pat. Nos. 5,324,633, 6,027,880, 5,585,639, and WO 00/12759; confocal excitation systems based on Nipkow discs, as described, for example, in U.S. Pat. No. 5,760,950; large-scale integrated fluorescence detection systems using micro-optics, as described, for example, in WO 99/27140; and laser scanning systems, as described, for example, in WO 00/12759. A general description of detection methods using such conventional detection systems can be found, for example, in U.S. Pat. No. 5,324,633.

In addition, as already described above, electrochemical detection methods may be used, for example by measuring the alteration of redox potentials via electrodes connected to the first surface and/or the second surface (see, e.g., Zhu, X. et al. (2004) Lab Chip. 4, 581-587) or by cyclic voltometry (see, e.g., Liu, J. et al. (2005) Anal. Chem. 77, 2756-2761; and Wang, J. (2003) Anal. Chem. 75, 3941-3945). Furthermore, an electric detection method can be employed, for example by impedance measurement (see, e.g. Radke, S. M. et al. (2005) Biosens. Bioelectron. 20, 1662-1667). Detection may also be accomplished by means of detecting acoustic surface waves, as described, e.g., in Z. Guttenberg et al. (2005) *Lab Chip.* 5, 308-317.

In specific embodiments of the present invention, detection is performed using FRET or BRET, which are based on the respective formation of fluorescence or bioluminescence quencher pairs, so that a fluorescence signal only occurs, if a target molecule has bound to a capture molecule immobilized on the porous matrix. The use of FRET is also described, e.g., in Liu, B. et al. (2005) *Proc. Natl. Acad. Sci. USA* 102, 589-593; and Szollosi, J. et al. (2002) *J. Biotechnol.* 82, 251-266. The use of BRET is detailed, for example, in Prinz, A. et al. (2006) *Chembiochem.* 7, 1007-1012; and Xu, Y. et al. (1999) *Proc. Natl. Acad. Sci. USA* 96, 151-156.

The invention is further described by the following figures and examples, which are solely for the purpose of illustrating specific embodiments of this invention, and are not to be construed as limiting the scope of the invention in any way.

DETAILED DESCRIPTION OF THE FIGURES

FIG. 1 depicts a schematic cross-sectional illustration of an assay device according to the present invention. The reaction chamber of the device is defined by the first surface, the second surface as well as the lateral sidewalls, wherein at least the central area of the second surface is made of an elastically deformable material. The device further comprises a displacer in form of a displacement body located opposite to the second surface. The distance between the first surface and the second surface is variable by applying pressure to the second surface via the displacer. The reaction chamber is located within a chamber body and sealed. An optical detection system is located opposite to first surface of the reaction chamber.

Figure 2:
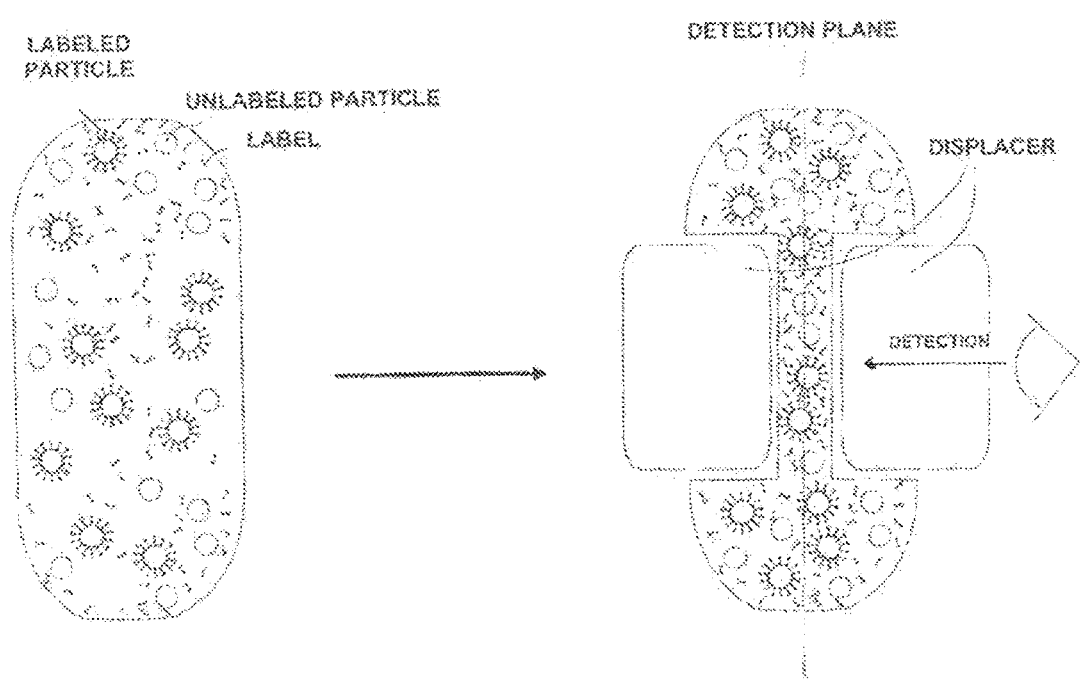
FIG. 2 is a schematic illustration of an inventive assay employing a device comprising two displacers located opposite relative to each other on different sides of the device.

FIG. 2 is a schematic illustration of an inventive assay employing a device comprising two displacers in form of displacement bodies. One of these displacers is located opposite to the first surface, the other one opposite to the second surface of the device. Furthermore, the displacers are positioned in such a way that they are located opposite relative to each other. The first surface and the second surface are made of an elastically deformable material at least in the respective surface areas located opposite to the displacers. A sample comprising multiple particles has been positioned within the reaction chamber along with a label having binding affinity for a particular species of particles. By applying pressure to the first surface and the second surface via the two displacers the distance between said surfaces becomes reduced in the central part of the reaction chamber thus causing an at least partial displacement of the sample within the reaction chamber (preferably to compensation zones not shown). In addition, by reducing said distance between the two surfaces a "gap" is formed in which detection of the specifically labeled particles takes place by recording a value indicative for their presence and/or number. Afterwards, it is preferred to re-increase the distance between the surfaces by resetting the two displacers to their original positions (i.e. by discontinuing applying pressure to the surfaces). The displaced sample will thus "move back" and becomes re-distributed throughout the reaction chamber before reducing the distance again. Determining the mean value of the results obtained during repeated detection steps performed within the "detection zone" will provide an accurate measure for the total number of the labeled particles to be detected within the entire reaction chamber (provided that the volumes of the reaction chamber as well as that of the "detection zone" are known).

Figure 3:
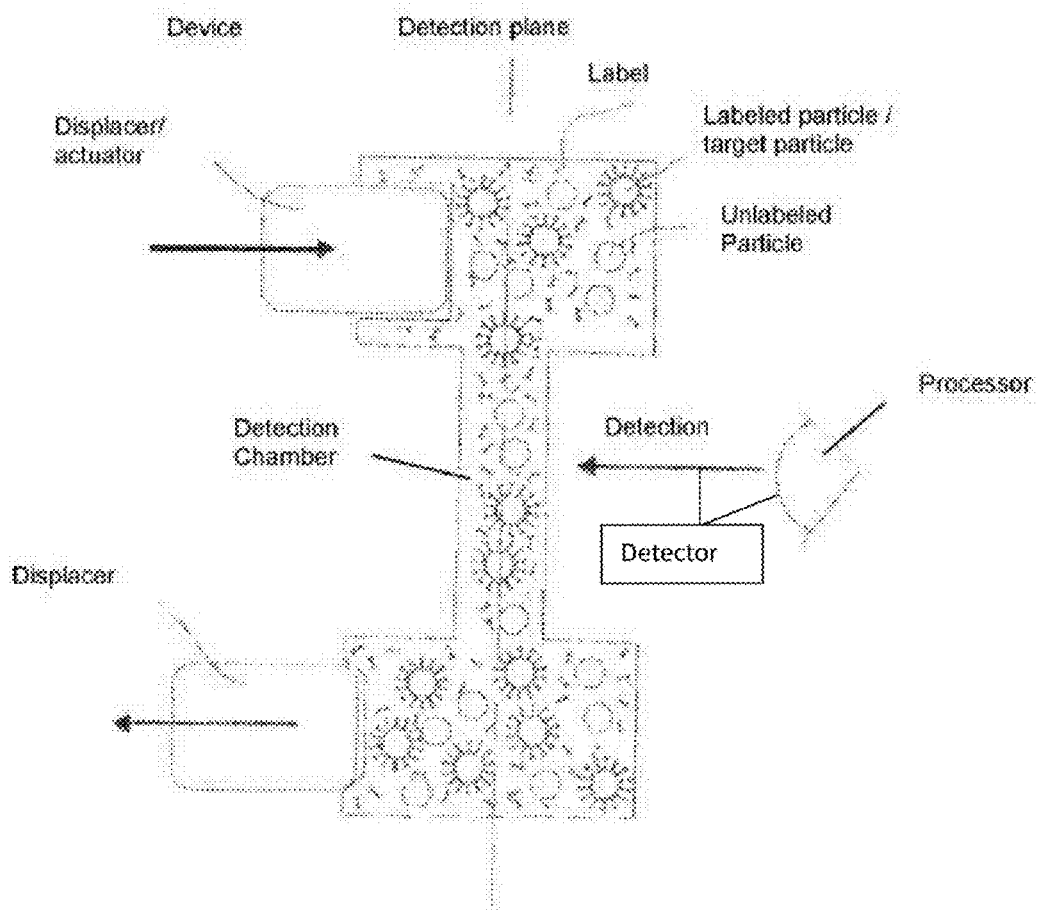
FIG. 3 is a schematic illustration of an inventive assay employing a device comprising two displacers located at different positions on the same of the device.

FIG. 3 is a schematic illustration of an alternative inventive assay employing a device comprising two displacers in form of displacement bodies that are located opposite to the same surface (referred to as the "first surface" below) at the two terminal regions of the device. The central part of the reaction chamber is configured as a capillary gap having a defined volume. The respective surface areas of the first surface located opposite the two displacers are made of an elastically deformable material. A sample comprising multiple particles has been positioned within the reaction chamber along with a label having binding affinity for a particular species of particles. By applying pressure to the first surface via the first displacer at one terminal region of the reaction chamber the distance between the first and the second surface becomes reduced in this part of the reaction chamber causing a displacement of the sample within the reaction chamber towards the other terminal region. Consequently, the respective second displacer located at the other terminal region is pushed by the displaced liquid backwards in its initial position resulting in an increase of the distance between the first surface and the second surface in this part of the reaction chamber. The displacement of the sample results in the positioning of a distinct subset of the labeled particles present in the reaction chamber within the capillary gap where detection takes place. By subsequently applying pressure to the first surface via the second displacer the sample is displaced within the reaction chamber in "backwards direction" resulting in the positioning of another distinct subset of the labeled particles within the capillary gap. Thus, by using the two displacers that are operated in opposite directions a continuous displacement, and thus also a mixing of the sample within the reaction chamber is achieved. By determining the mean value of the results obtained during repeated detection steps performed within the "detection zone" the total number of the labeled particles to be detected within the entire reaction chamber can be calculated (provided that the volume of the reaction chamber is known as well).

Figure 4A:
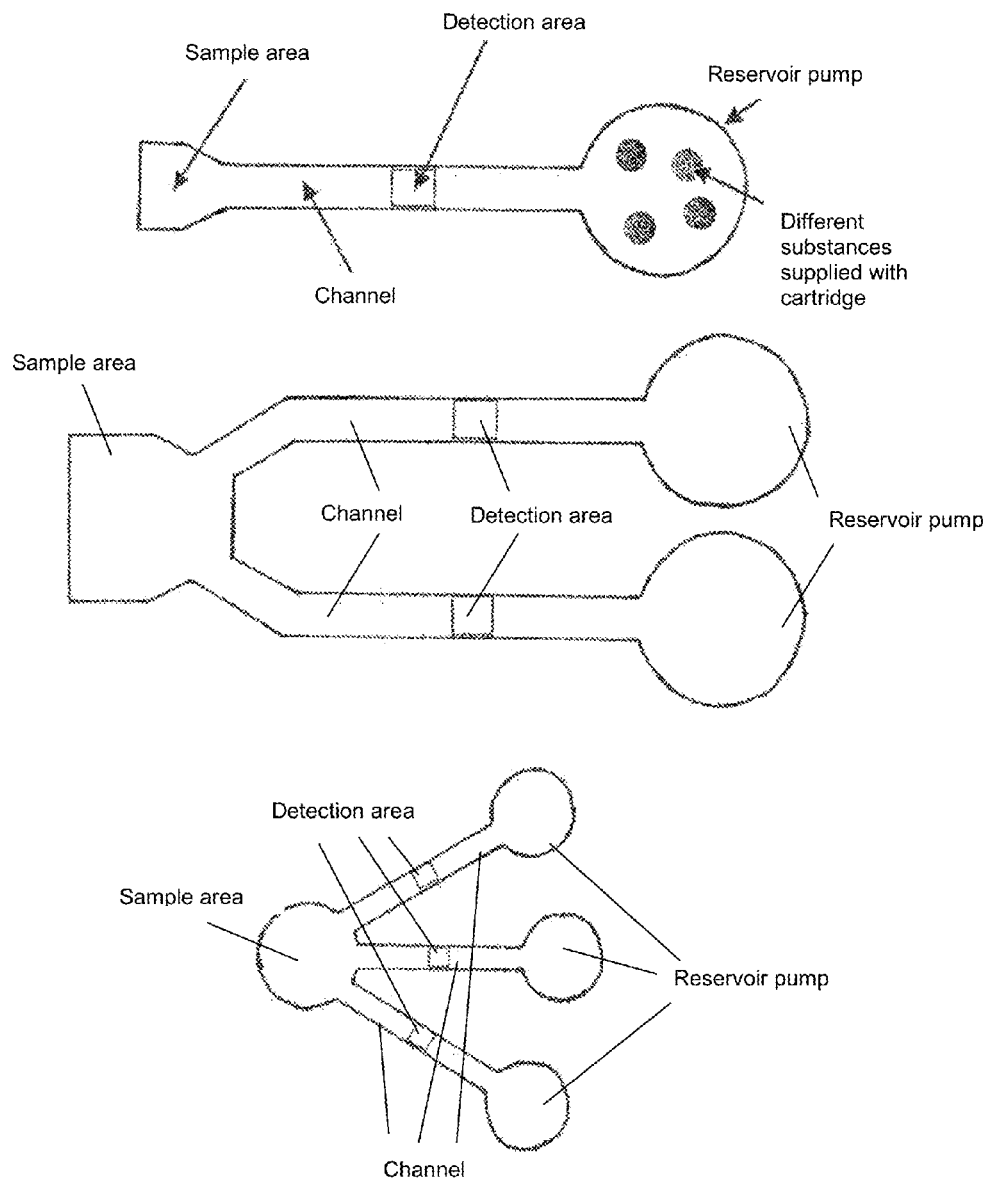

FIG. 4 illustrates a specific embodiment of inventive devices and systems as well as the corresponding mode of operation. FIG. 4A (top panel) schematically depicts a singular device or part which is configured as a channel defined by a first surface and a second surface and running out at one end in a compensation zone or reservoir. At least part of the reservoir is made of an elastically deformable material. Within said reservoir reagents (such as buffers or labels) may be provided, preferably in dry form. A displacer is located opposite to one surface of the reservoir (not shown). At the opposite end of the device a sample introduction passage (i.e. a sample loading zone) is provided. The channel encompasses a particular detection area (i.e. a detection zone). At least two such devices or parts may be assembled to a multipart system comprising separate reaction chambers in order to perform multiple assays of one-sample in parallel. The respective reaction chambers are in communication with each other via a common sample introduction passage. FIG. 4A (middle and bottom panel) depicts two exemplary embodiments of such a multipart system comprising two and three devices, respectively. FIG. 4B schematically illustrates how the unit (either as a single device or as part of a multipart system) is operated. The upper panel is a cross-sectional view of the device in its initial state. The channel encompassing a particular detection area is delimited by a rigid first surface (hatched) and a second surface made of an elastically deformable material ("cover membrane"). A displacer ("stencil") is pressed towards the second surface of the reservoir resulting in a reduction of the distance between the first surface and the second surface in this surface area, preferably to a value of zero or almost zero. A drop of a liquid sample is placed in the sample introducing passage and introduced into the reaction chamber by means of negative pressure resulting from a release of the displacer (i.e. by moving it in backwards direction), thus causing a relaxation of the reservoir (FIG. 4B, middle panel). Finally, the displacer is again pressed towards the second surface of the reservoir. Thus, by another reduction of the distance between the two surfaces in this surface area the sample becomes at least in part displaced within the reaction chamber. Therefore, by repeating the consecutive compression and relaxation of the reservoir an agitation/mixing of the sample can be accomplished before detection of one or more species of particles is performed (FIG. 4B, lower panel).

Figure 5:
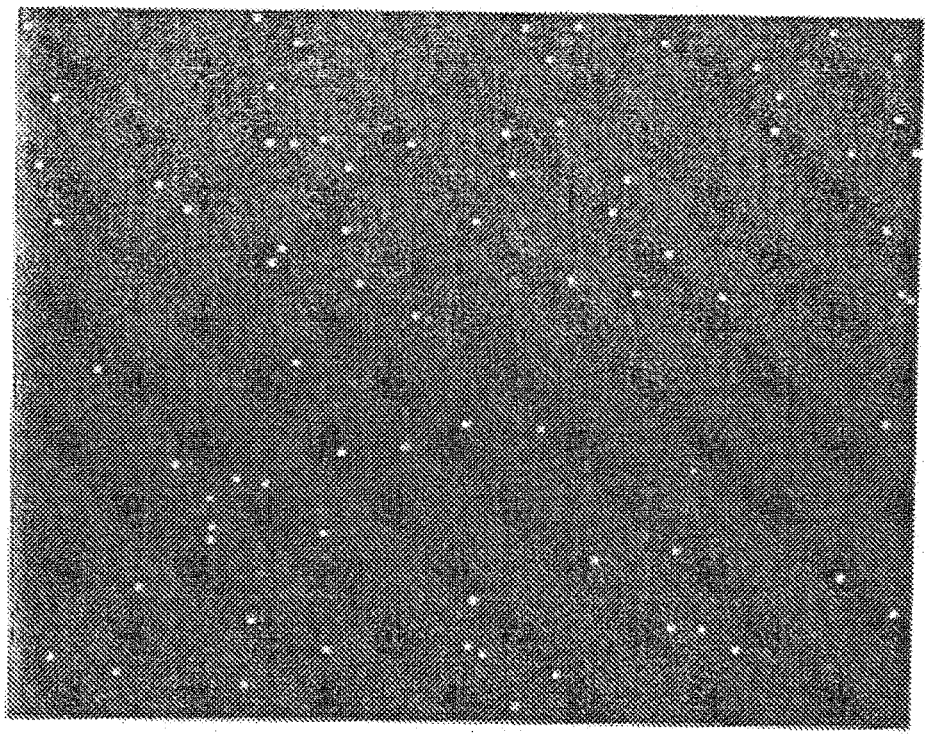
FIG. 5 depicts the results of an assay according to the invention for determining the number of CD4+ cells in human blood.

FIG. 5 depicts the results of an assay according to the invention for determining the number of CD4+ cells in human blood. The CD4+ cells of a human blood sample were labeled with an anti-CD4 phycoerythrin-conjugated monoclonal antibody using the CD3CD4 kit (GE Healthcare Life Sciences, Heidelberg, Germany) according to the instructions of the manufacturer. The blood sample was diluted to a concentration of less than 500 cells/µl and analyzed in a reaction chamber configured as a capillary channel that is made of polydimethylsiloxane. The reaction chamber has a total volume of approximately 2 µl. After introducing the sample into the reaction chamber by means of capillary forces it was agitated by applying pressure to one surface of the reaction chamber via a tappet thus causing a partial displacement of the sample. Displacing the sample in such manner was repeated 10 times. The labeled cells were analyzed by means of optical detection using a microscope (Akioskop; Carl Zeiss GmbH, Jena, Germany) with a 10× objective (image field 1727×1385 µm) and an F1-FITC filter (Zeiss #09). The exposure rime was 2500 ms. Detection was repeated 5-7 times. A representative microscope image is shown. The number of CD4+ cells in the sample was determined using an appropriate computer software package (Image J software version 1.71, a public domain Java image processing program inspired by NIH Image) by calculating the mean value of the cell numbers obtained for the individual measurements. Since the image field and thus the volume of the "detection zone" as well as the volume of the reaction chamber were known, the concentration of CD4+ cells/µl sample could be calculated.

Figure 6:
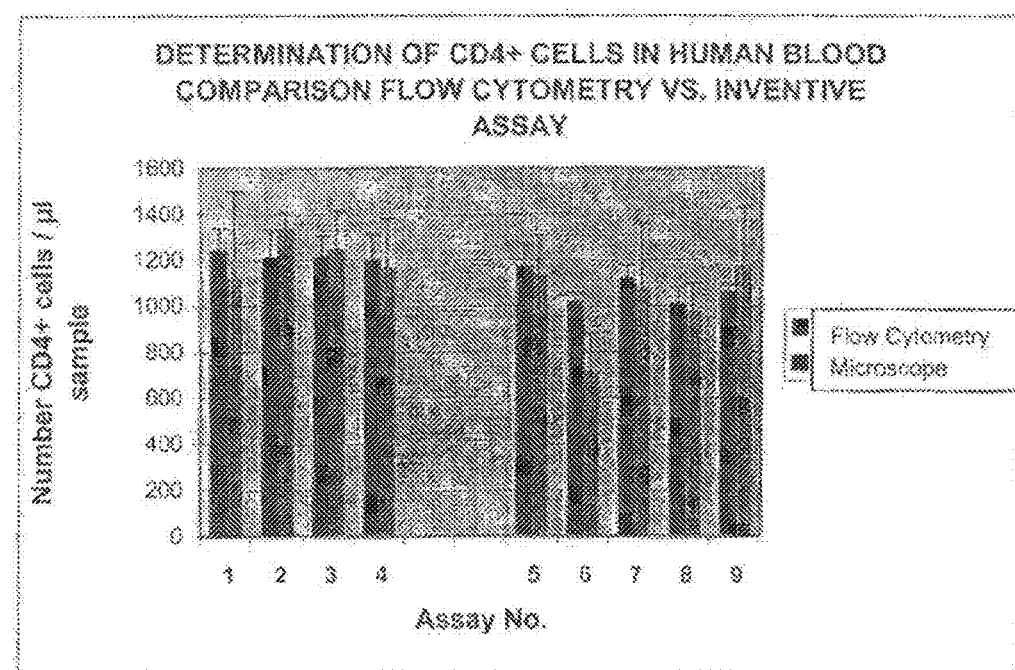
FIG. 6 depicts a comparison of CD4+ cell numbers in human blood as obtained by flow cytometry and an assay according to the invention, respectively.

FIG. 6 depicts a comparison of CD4+ cell numbers in human blood as obtained by flow cytometry and an assay according to the invention, respectively. The CD4+ cells of a human blood sample were labeled as described in FIG. 5. Samples were analyzed using a Guava PCA flow cytometer (Guava Technologies, Inc., Hayward, Calif., USA; excitation wavelength: 532 nm, emission wavelength: 580-583 nm) according to the manufacturer's instructions as well as by an inventive assay as described in FIG. 5. The results are mean values±SEM of 5-7 measurements and are expressed as numbers of CD4+ cells per µl blood.

EXAMPLES

Example 1

Determining the Presence or CD4+ Cells in Human Blood

The CD4+ cells of a human blood sample were labeled with anti-CD4 phycoerythrin-conjugated monoclonal antibody (CD4-PE) using the CD3CD4 kit (GE Healthcare Life Sciences. Heidelberg, Germany) according to the instructions of the manufacturer. In brief, 10 µl blood were mixed with 2 µl CD4-PE (1:25 diluted stock solution) and 2 µl 20 mM EDTA. Then, the mixture was incubated for 15 min in the dark.

The blood sample was diluted to a concentration of less than 500 cells/µl (a higher concentration would interfere with proper handling of the device) and analyzed in a reaction chamber configured as a capillary channel that is made of polydimethylsiloxane, i.e. an elastically deformable material. The reaction chamber is 2.048 mm×0.04 mm×24 mm in size and thus has a total volume of approximately 2 µl.

For introducing the sample 2.5 µl of the diluted blood sample were placed adjacent to the opening of the channel and introduced by capillary forces without further external manipulation. Afterwards, the reaction chamber was agitated by applying pressure to one surface of the reaction chamber via a tappet (or a forceps) thus causing a partial displacement of the sample. Displacing the sample in such manner was repeated 10 times.

The labeled cells were analyzed by means of optical detection using a microscope (Akioskop; Carl Zeiss GmbH, Jena, Germany) with a 10× objective (image field 1727× 1385 µm) and an F1-FITC filter (Zeiss #09). The exposure rime was 2500 ms. Detection was repeated 5-7 times. A representative microscope image is shown in FIG. 5.

The number of CD4+ cells in the sample was determined using an appropriate computer software package (Image J software version 1.71, a public domain Java image processing program inspired by NIH Image) by calculating the mean value of the cell numbers obtained for the individual measurements. Since the image field and thus the volume of the "detection zone" as well as the volume of the reaction chamber were known, the concentration of CD4+ cells/µl sample could be calculated.

Example 2

Comparison of Flow Cytometry and an Inventive Assay for Determining the Number of CD4+ Cells in Human Blood In order to test the suitability of the inventive assay for quantitative analyses it was compared to conventional flow cytometry for determining CD4+ cell numbers in human blood. The CD4+ cells of a human blood sample were labeled as described in Example 1. Samples were analyzed using a Guava PCA flow cytometer (Guava Technologies, Inc., Hayward, Calif. USA; excitation wavelength: 532 nm, emission wavelength: 580-583 nm) according to the manufacturer's instructions as well as by an inventive assay as described in Example 1. The results are shown in FIG. 6 and represent mean values±SEM of 5-7 measurements. The results are expressed as numbers of CD4+ cells per µl blood.

The mean values obtained for the two methods as well as the respective differences in percent are also summarized in the following table;

| Assay no. | Mean Flow | Mean Assay | Δ [%] |
|---|---|---|---|
| 1 | 1234 | 1114 | 9.78 |
| 2 | 1208 | 1330 | 9.14 |
| 3 | 1212 | 1245 | 2.66 |
| 4 | 1198 | 1162 | 3.01 |

-continued

| Assay no. | Mean Flow | Mean Assay | Δ [%] |
|---|---|---|---|
| 5 | 1169 | 1131 | 3.34 |
| 6 | 1011 | 710 | 29.83 |
| 7 | 1118 | 1064 | 4.85 |
| 8 | 1008 | 968 | 4.03 |
| 9 | 1058 | 1170 | 9.58 |

As can be seen, in five of the nine independent assays performed the variation between the two methods is less than 5%, in three cases it is less than 10%. Only in assay no. 6 a higher variation of about 30% has been obtained which may be result from the fact that in this case the two analyses have not been performed in parallel, i.e. with identical blood samples. The other results, however, clearly indicate the suitability of the inventive method for the quantitative detection of particles in biological samples.

The present invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A device, comprising:
    a detection chamber that receives a sample comprising multiple labelled particles,
    an actuator that displaces some of the multiple labelled particles from the detection chamber comprising a first surface and a second surface opposite to the first surface and comprising an area made of an elastically deformable material so that only a first subset of the multiple labelled particles remains in the chamber as a result of the elastically deformable material,
    a detector including an optical system that detects particles of the first subset of labelled particles,
    a processor that determines, based on the detected particles, a value indicative of the number of particles of the first subset of particles and to determine the number or abundance of particles in the sample based on the number of particles of the proper subsets.

2. The device of claim 1, wherein the processor operates the actuator to (a) reintroduce at least some of the displaced multiple labelled particles to the detection chamber and, subsequently, (b) displace some of the multiple labelled particles from the detection chamber so that only a second subset of the multiple labelled particles remains and operates the detector to detect particles of the second subset and determine, based on the detected particles, the number of particles of the second subset of particles.

3. The device of claim 1, further comprising a reservoir capable of receiving particles displaced from the detection chamber and from which particles can be reintroduced to the detection chamber.

4. The device of claim 3, wherein the reservoir comprises an expandable wall.

5. The device of claim 1, wherein the processor determines a value indicative of a number or abundance of particles in the sample based on the value indicative of the number of particles of the subset.

6. The device of claim 1, further comprising a reaction chamber comprising a capillary gap defining a volume.

7. The device of claim 1, further comprising one or more displacers configured to apply pressure to the elastically deformable material.

8. The device of claim 7, wherein the one or more displacers are located opposite to the first surface and/or of the second surface.

9. The device according to claim 1, wherein the first surface and/or the second surface comprise(s) a surface area where detection takes place.

10. The device according to claim 1, wherein at least one or more parts of the first surface and/or of the second surface is/are elastically deformable.

11. The device according to claim 1, wherein at least a part of the first and/or the second surface is/are made of a transparent material.

12. The device according to claim 1, wherein the distance between the first and the second surface is variable in a range of 0 mm to 1 mm.

13. The device according to claim 1, wherein the reaction chamber includes elastic sidewalls laterally delimiting the reaction chamber.

14. The device according to claim 1, wherein the detector includes an optical system.

15. A device, comprising:
    a detection chamber that receives a sample comprising multiple labelled particles,
    an actuator that displaces some of the multiple particles from the detection chamber comprising a first surface and a second surface opposite to the first surface and comprising an area made of an elastically deformable material so that only a first subset of the multiple labelled particles remains in the chamber,
    a detector including an optical system that detects particles of the first subset of labelled particles, and
    a processor that determines, based on the detected particles, the presence of a target particle among particles of the first subset of particles.

* * * * *